(12) United States Patent
Aronson

(10) Patent No.: US 12,390,111 B2
(45) Date of Patent: *Aug. 19, 2025

(54) UNIVERSAL HEALTH METRICS MONITORS

(71) Applicant: Jeffry David Aronson, Austin, TX (US)

(72) Inventor: Jeffry David Aronson, Austin, TX (US)

(*) Notice: Subject to any disclaimer, the term of this patent is extended or adjusted under 35 U.S.C. 154(b) by 188 days.

This patent is subject to a terminal disclaimer.

(21) Appl. No.: 17/984,266

(22) Filed: Nov. 10, 2022

(65) Prior Publication Data

US 2023/0071230 A1  Mar. 9, 2023

Related U.S. Application Data

(63) Continuation-in-part of application No. 17/568,083, filed on Jan. 4, 2022, now Pat. No. 11,527,332, which
(Continued)

(51) Int. Cl.
*A61B 5/00* (2006.01)
*A61B 5/0205* (2006.01)

(52) U.S. Cl.
CPC .......... *A61B 5/0077* (2013.01); *A61B 5/0205* (2013.01)

(58) Field of Classification Search
CPC .............. A61B 5/0077; A61B 5/0205; A61B 2562/0204; A61B 2562/0271; A61B 5/01;
(Continued)

(56) References Cited

U.S. PATENT DOCUMENTS

| | | | |
|---|---|---|---|
| 2007/0005311 A1* | 1/2007 | Wegerich | G05B 23/0254 703/2 |
| 2011/0040574 A1* | 2/2011 | Fung | H04L 63/04 713/168 |

(Continued)

OTHER PUBLICATIONS

Liu et al., "Evaluation of Learning Algorithms for Optimal Policy Representation in Sensor-Network Based Human Health Monitoring Systems", 7th International Conference on Information, Communications and Signal Processing, Dec. 2009, pp. 1-5 (Year: 2009).*

*Primary Examiner* — Kenneth W Chang
(74) *Attorney, Agent, or Firm* — Kowert, Hood, Munyon, Rankin & Goetzel, P.C.; Brian E. Moore

(57) ABSTRACT

Scalable, configurable, complete spectrum universal health metrics monitors and bicorders are disclosed that record data or make selected determinations from a complete spectrum of health determinations regarding or utilizing sensor observations of people. Universal health metrics monitors utilize necessary resources and predetermined criteria in their making of selected health determinations. Universal health metrics monitors may utilize measure points in their locating of selected analytically rich aspects, characteristics, or features of or from sensor observation-derived representations, Universal health metrics monitors assign appropriate informational representations to selected analytically rich aspects, characteristics, features, or measure points, which are stored in datasets where they can be utilized in real-time or thereafter by universal health metrics monitors in their making of selected health determinations regarding or utilizing sensor observations or people who are subjects of sensor observations.

22 Claims, 2 Drawing Sheets

Related U.S. Application Data is a continuation-in-part of application No. 17/165,191, filed on Feb. 2, 2021, now Pat. No. 11,238,992, which is a continuation-in-part of application No. 16/891,080, filed on Jun. 3, 2020, now Pat. No. 10,943,693, which is a continuation-in-part of application No. 15/981,785, filed on May 16, 2018, now Pat. No. 10,943,097.

(60) Provisional application No. 62/507,128, filed on May 16, 2017.

(58) Field of Classification Search
CPC . A61B 5/02055; A61B 5/0261; A61B 5/1114; A61B 5/1121; A61B 5/445; A61B 5/6898; A61B 5/7264; A61B 5/7275; Y02A 90/10
See application file for complete search history.

(56) References Cited

U.S. PATENT DOCUMENTS

| | | | | |
|---|---|---|---|---|
| 2011/0124982 | A1* | 5/2011 | Pipke | A61B 5/0205 600/301 |
| 2014/0324459 | A1* | 10/2014 | Barfield | G16H 40/67 705/3 |
| 2016/0379511 | A1* | 12/2016 | Dawson | G06T 11/206 434/362 |

\* cited by examiner

UNIVERSAL HEALTH METRICS MONITORS

CROSS-REFERENCE TO RELATED APPLICATIONS

This application is a continuation-in-part application of U.S. patent application Ser. No. 17/568,083, filed Jan. 4, 2022, entitled "Sensor Data Analyzing Machines", having the same inventor, now allowed, which is incorporated herein by reference in its entirety; which application is a continuation-in-part application of U.S. patent application Ser. No. 17/165,191, filed Feb. 2, 2021, issued as U.S. Pat. No. 11,283,992 on Feb. 1, 2022, entitled "Configurable Concise Datasets Platform", having the same inventor, which is incorporated herein by reference in its entirety; which application is a continuation-in-part application of U.S. patent application Ser. No. 16/891,080, filed Jun. 3, 2020, issued as U.S. Pat. No. 10,943,693 on Mar. 9, 2021, entitled "Concise Datasets Platform", having the same inventor, which is incorporated herein by reference in its entirety; which application is a continuation-in-part application of U.S. patent application Ser. No. 15/981,785, filed May 16, 2018, issued as U.S. Pat. No. 10,943,097 on Mar. 9, 2021, entitled "Scalable Configurable Universal Full Spectrum Cyber Process That Utilizes Measure Points From Sensor Observation-Derived Representations or Analytically Rich Sparse Data Sets For Making Cyber Determinations Regarding or Utilizing Sensor Observations or Sensor Observation Subjects", having the same inventor, which is incorporated herein by reference in its entirety; which application claims the benefit of priority from U.S. provisional application No. 62/507,128, entitled "Scalable Universal Full Spectrum Cyber Determining Process That May Utilize Reference Points Located On Sensor-Observation-Derived Representations", having the same inventor, which was filed May 17, 2017, and which is incorporated herein by reference in its entirety.

BACKGROUND OF THE DISCLOSURE

Over the past several years a broad spectrum of fields have experienced great advantages from their collection, analysis, and utilization of data. However, in the same several years, there has been very little increase in the collection, analysis, and utilization of health-related sensor data. Therefore, prior art healthcare still provides only a very limited number of the possible sensor data-enabled health services and benefits.

Universal Health Metrics Monitors are configurable for providing a complete spectrum of the health-related services and benefits that can be derived from the analysis of sensor data.

SUMMARY OF THE DISCLOSURE

Unless otherwise specified herein, throughout this entire disclosure, use of any singular form of any word, phrase, or statement indicates either the singular or the plural form of the word, phrase, or statement, and use of any plural form of any word, phrase, or statement indicates either the singular or the plural form of the word, phrase, or statement. Additionally, the term "or" shall be construed as the logically inclusive "or". Hence, the statement "A or B" shall be true if: (a) only A is true, (b) only B is true, and (c) both A and B are true; the notation "A and/or B" explicitly refers to the logically inclusive "or".

The disclosed scalable, configurable, complete spectrum, universal health metrics monitors utilize data from sensor observations in their making of or reporting on selected health determinations regarding or utilizing sensor-observed analytically rich aspects, characteristics, or features of people's health.

Universal health metrics monitors are configurable for utilizing measure points in their locating of selected analytically rich aspects, characteristics, or features of or from sensor observation-derived representations of sensor observations or sensor observation subjects.

When the determinations that are to be made by universal health metrics monitors have been selected, then further determinations are made regarding which analytically rich aspects, characteristics, or features of or from sensor observation-derived representations can or will be used for accurately or reliably making selected determinations regarding a person's health.

Universal health metrics monitors are configurable for reliably making selected determinations regarding a person's health through utilization of (a) information, (b) data from sensor observations, or (c) data that were derived from the processing of information or data from sensor observations.

Using data from an oximeter, thermometer, and 360-degree motion detector, universal health metrics monitors can be configured to determine, for example, the earliest sensor-detectable moment that a person has a particular strain of the flu. This is just one of many aspects, characteristics, or features of a person's health that health metrics monitors can determine.

Universal health metrics monitors are configurable for utilizing a combination of changes that occur over time to sensor data regarding a person's temperature, range of blood oxygenation, respiration patterns, body movement, cough, or tremors to reliably indicate that the person has the earliest sensor-detectable onset of a particular strain of flu.

Universal health metrics monitors are configurable for employing tools, methodologies, or programming from a complete spectrum of tools, methodologies, or programming that can be utilized in their making of selected determinations regarding a person's health.

Universal health metrics monitors are configurable for utilizing one measure point in the locating of a pulse point on a sensor observation-derived representation of a specific person's face. A scalable configurable grid is utilized for structuring a twenty-one pixel by twenty-one-pixel square with the single measure point at its center. The sums of the measurements of observed levels of red, green, or blue light from each column or from each row of pixels from within the scalable configurable grid are stored as data that can be utilized by universal health metrics monitors in their making of determinations that heartbeats/pulses have occurred.

In addition, universal health metrics monitors are configurable for utilizing the sums from one or more columns or rows from the scalable configurable grids in their making of determinations regarding a specific person's blood pressure.

Data are stored in datasets for utilization in the making of selected determinations regarding the health of a person. These determinations can be made by universal health metrics monitors in real time or at times thereafter. Universal health metrics monitors are configurable for having no further use for original sensor observation datasets when all necessary data have been included in datasets. At this point in the operations of universal health metrics monitors, original sensor observation datasets can be deleted or stored for later use.

Universal health metrics monitors are configurable for comparing data from first-series sensor observations of known analytically rich aspects, characteristics, or features of or from sensor observations or people who are sensor observation subjects to data from second-series sensor observations of yet-to-be-identified analytically rich aspects, characteristics, or features of or from second-series sensor observations or sensor observation subjects.

For universal health metrics monitors to utilize informational representations from datasets in their making of selected determinations regarding the health of a person, their processing of the first-series observations and their processing of the second-series observations of the same subject should result in their assignments of essentially the same standard informational representations to many aspects, characteristics or features from both sensor observations. Universal health metrics monitors are configurable for utilizing the same standard tools, methodologies, or programming in the processing of second-series observations as were used in the processing of the first-series observations to which they will be compared.

Using working datasets that contain only one pulse point-located measure point per image is an example of how universal health metrics monitors can be configured to utilize "a best performing blend of as simple, concise, and efficient as possible" as a strategy for all or part of their operations.

Universal health metrics monitors, through their utilization of measure points or concise datasets, are configurable for accurately or reliably making selected determinations regarding people's health from a complete spectrum of health determinations that can be made regarding or utilizing sensor observations or people who are subjects of sensor observations.

Tools, methodologies, and programming of universal health metrics monitors can be configured to accurately or reliably make selected determinations regarding people's health. These tools, methodologies, and programming enable universal health metrics monitors to achieve best performance while also remaining as simple, concise, and efficient as possible.

The present disclosure pertains to scalable, configurable, complete spectrum, universal health metrics monitors;

universal health metrics monitors comprise or utilize resources that include: (a) computing devices, (b) bicorders, (c) tools, (d) methodologies, (e) programming, (f) information, (g) selected criteria, (h) data, and (i) other necessary resources;

universal health metrics monitors' resources are from a complete spectrum of resources that can be used as parts of universal health metrics monitors, or as parts of universal health metrics monitors' operations;

universal health metrics monitors, parts thereof, or operations thereof, can be utilized for purposes from a complete spectrum of purposes for which universal health metrics monitors, parts thereof, or operations thereof, can be utilized;

a complete spectrum of purposes for which universal health metrics monitors, parts thereof, or parts of operations thereof can be utilized includes capturing, recording, or monitoring all or selected parts of sensor observations of analytically rich aspects, characteristics, or features of people's health;

universal health metrics monitors are configurable for making or reporting on selected health determinations regarding or utilizing sensor-observed analytically rich aspects, characteristics, or features of people's health;

universal health metrics monitors are configurable for making health determinations from a complete spectrum of health determinations that can be made regarding or utilizing analytically rich aspects, characteristics, or features of or from sensor observation-derived representations of people;

a complete spectrum of cyber determinations regarding or utilizing analytically rich aspects, characteristics, or features of or from sensor observation-derived representations of people includes determinations that identify health-related tells; the health-related tells are regarding or utilizing analytically rich aspects, characteristics, or features of or from sensor observation-derived representations of people, the tells can be utilized by universal health metrics monitors in their accurate or reliable making of selected health-related determinations, that a specific person may, should, or does want to utilize or be made aware of, regarding selected health-related occurrences that the specific person has, had, or will have;

the tells are from a complete spectrum of sensor-observable tells regarding people's health;

the tells are utilizable by universal health metrics monitors in their making of selected determinations regarding or utilizing selected sensor-observed analytically rich aspects, characteristics, or features of people's health;

selected determinations are utilizable by universal health metrics monitors in their monitoring of, identifying, or reporting on, selected sensor-observed analytically rich aspects, characteristics, or features of or from people's health;

monitoring operations of universal health metrics monitors or recording operations of bicorders can be made: (a) as one-time, single events, (b) intermittently, or (c) constantly;

reporting operations of universal health metrics monitors are configurable for making reports from a complete spectrum of reports that can be made regarding or utilizing analytically rich aspects, characteristics, or features of or from sensor observation-derived representations of people's health;

recordings are made of all or parts of selected sensor observation data;

people, universal health metrics monitors, or other devices select all or the parts of selected sensor observation data that are to be recorded or utilized;

universal health metrics monitors are configurable for including, in datasets, all or the selected parts of sensor observation data;

sensor observations are made at points in time or over periods of time;

any other necessary resources can include sensors that are utilizable by universal health metrics monitors in their observing of selected analytically rich aspects, characteristics, or features of people's health;

sensors are from a complete spectrum of sensors that can be utilized for observing analytically rich aspects, characteristics, or features of people's health;

the complete spectrum of sensors includes: (i) internal sensors, (ii) external sensors, (iii) wearable sensors, (iv) sensors that are in an observable proximity of people who are subjects of sensor observations, or (v) other sensors that are utilizable in making selected determinations regarding or utilizing people's health.

bicorders record all or selected parts of data from sensor observations that are utilized by universal health metrics monitors;

bicorders can be (a) virtual devices, physical devices, or combinations thereof, (b) integral parts of universal health metrics monitors, (c) devices that are not parts of universal health metrics monitors, or (d) parts of one or more other devices or systems;

computing devices can be virtual devices, physical devices, or combinations thereof;

physical computing devices include tangible non-transient memory devices and input devices or output devices;

universal health metrics monitors are configurable for utilizing all or part of their resources for (a) selecting or deriving data that are included in datasets, or (b) utilizing concise datasets in the making of selected sensor data-based determinations regarding the health of people who are subjects of sensor observations;

universal health metrics monitors are configurable for utilizing concise datasets in their making of selected determinations regarding the health of people who are subjects of sensor observations;

concise datasets are utilizable for purposes from a complete spectrum of purposes for which concise datasets can be utilized;

concise datasets include selected sensor data or derived data;

selected sensor data include informational representations that were selected from sensor observation datasets;

derived data include informational representations that were derived from processing (i) informational representations that were selected from sensor observation datasets, or (ii) informational representations that were selected from derived data;

selected sensor data or derived data are utilizable by universal health metrics monitors in their making of selected determinations regarding people's health;

universal health metrics monitors utilize selected tools, methodologies, or programming for processing derived data; these tools, methodologies, or programming are from a complete spectrum of tools, methodologies, or programming that can be utilized to derive data for or from concise datasets;

universal health metrics monitors are configurable for utilizing measure points in their locating of selected analytically rich aspects, characteristics, or features of or from sensor observation-derived representations of people;

measure points are utilizable by universal health metrics monitors in their making of selected determinations regarding sensor observations or people's health;

universal health metrics monitors assign appropriate informational representations to measure points and to selected analytically rich aspects, characteristics, or features of or from sensor observation-derived representations that are located through utilization of measure points;

analytically rich aspects, characteristics, or features of or from sensor observations or people who are subjects of sensor observations are from a complete spectrum of analytically rich aspects, characteristics, or features of or from sensor observations or people who are subjects of sensor observations;

analytically rich aspects, characteristics, or features of or from measure points are from a complete spectrum of analytically rich aspects, characteristics, or features of or from measure points;

determinations are from a complete spectrum of health determinations that can be made regarding or utilizing sensor observations, people who are subjects of sensor observations, or measure points;

a complete spectrum of determinations regarding or utilizing sensor observations, people who are subjects of sensor observations, or measure points includes determinations that identify tells that are utilizable by universal health metrics monitors in their accurate or reliable making of selected determinations regarding or utilizing sensor observations, the health of people who are subjects of sensor observations, or measure points;

tells are from a complete spectrum of sensor-observable tells regarding or utilizing sensor observations, people who are subjects of sensor observations, or measure points;

selected determinations are utilizable for purposes from a complete spectrum of purposes for which determinations regarding or utilizing sensor observations, the health of people who are subjects of sensor observations, or measure points can be utilized;

universal health metrics monitors are configurable for making selected health determinations in real time or at times thereafter;

universal health metrics monitors are configurable for making at least one member selected from the group consisting of (1) one-time, single event determinations regarding or utilizing sensor observations, the health of people who are subjects of sensor observations, or measure points, (2) intermittently provided determinations regarding or utilizing sensor observations, the health of people who are subjects of sensor observations, or measure points, and (3) constantly provided determinations regarding or utilizing sensor observations, the health of people who are subjects of sensor observations, or measure points;

universal health metrics monitors utilize information from a complete spectrum of information that can be utilized by universal health metrics monitors in their selecting, deriving, or processing of data for or from datasets, or their making of selected health determinations;

a complete spectrum of information includes information from sensor observations;

information is from points in time or over periods of time;

sensor observations are made by sensors from a complete spectrum of sensors that can be utilized by universal health metrics monitors in their making of selected determinations regarding people's health;

universal health metrics monitors are configurable and all or parts of their resources or operations can be configured for utilization in one or more configurations;

universal health metrics monitors are scalable, regarding included or utilized health metrics monitor resources, to fall at a point in a range of, from a minimum to a maximum, wherein at the minimum, universal health metrics monitors are scaled to only include or utilize resources that are needed in their making of least complex selected determinations, regarding included or utilized health metrics monitor resources, and wherein at maximum, universal health metrics monitors are scaled to include or utilize all health metrics monitor resources;

sensor observations or people who are subjects of sensor observations are from a complete spectrum of sensor observations or people who are subjects of sensor observations; and universal health metrics monitors further comprise and utilize in any sequence at least one part of at least one operation from a group consisting of (a) first-series observation operations, wherein universal health metrics monitors are configured for utilizing first-series sensor observations; wherein first-series sensor observations or people who are subjects of first-series sensor observations have previously determined analytically rich aspects, characteristics, or features; the universal health metrics monitors recognize the previously determined aspects, characteristics, or features; the universal health metrics monitors assign appropriate informational representations regarding the recognized aspects, characteristics, or features of or from the sensor observations or the people; the assigned informational representations are utilizable by the universal health metrics monitors in their making of selected determinations regarding or utilizing the sensor observations or the people's health; the universal health metrics monitors include assigned informational representations of or from the first-series observations in first-series observation datasets, (b) second-series observation operations, wherein the universal health metrics monitors are configured for utilizing second-series sensor observations; wherein second-series sensor observations or people who are subjects of second-series sensor observations have selected yet-to-be-determined analytically rich aspects, characteristics, or features; the universal health metrics monitors recognize the yet-to-be-determined analytically rich aspects, characteristics, or features; the universal health metrics monitors assign appropriate informational representations regarding the yet-to-be-determined analytically rich aspects, characteristics, or features of or from the sensor observations or the people; the assigned informational representations are utilizable by the universal health metrics monitors in their making of the selected determinations regarding or utilizing the sensor observations or the people's health; the universal health metrics monitors include assigned informational representations of or from the second-series observations in second-series observation datasets, (c) measure point operations, wherein universal health metrics monitors utilize measure points in their locating of selected analytically rich aspects, characteristics, or features of or from sensor observation-derived representations of sensor observations or people who are subjects of sensor observations; wherein universal health metrics monitors assign appropriate informational representations regarding the measure points or the selected analytically rich aspects, characteristics, or features; wherein the informational representations are stored or utilized by the universal health metrics monitors in their making of selected determinations regarding or utilizing the sensor observations or the people's health, (d) concise datasets operations, wherein universal health metrics monitors select, derive, or utilize data for or from concise datasets; wherein the concise datasets include selected sensor data or derived data; wherein the selected sensor data includes informational representations from sensor observation datasets; and wherein the derived data is comprised of informational representations that were derived from (i) processing of selected informational representation from the sensor observation data, or (ii) processing of selected informational representations from the derived data; wherein informational representations from the selected data or the derived data are utilizable by universal health metrics monitors in their making of selected determinations regarding or utilizing sensor observations or people's health, (e) matching operations, wherein universal health metrics monitors match selected informational representations from second-series observations to comparable informational representations from first-series observations, (f) comparing operations, wherein universal health metrics monitors make comparisons of selected informational representations from second-series observations to selected informational representations from first-series observations; wherein the universal health metrics monitors utilize data from comparisons (i) for providing conclusions, or (ii) in their making of selected determinations, (g) determining operations, wherein universal health metrics monitors utilize conclusions from comparing operations or information in their making of selected determinations regarding or utilizing sensor observations or the health of people who are subjects of sensor observations, and (h) reporting operations, wherein universal health metrics monitors make selected reports regarding or utilizing aspects, characteristics, or features of or from their operations.

In some embodiments, universal health metrics monitors are further configurable for utilizing (a) tools, (b) methodologies, (c) programming, (d) people, or (e) combinations thereof for selecting aspects, characteristics, or features of or for their operations; the tools, methodologies, and programming are from a complete spectrum of tools, methodologies, and programming that can be utilized for selecting aspects, characteristics, or features of or for operations of universal health metrics monitors.

In some embodiments, universal health metrics monitors are further configurable for utilizing at least one member selected from the group consisting of (a) tools, (b) methodologies, (c) programming, (d) data, (e) information, (f) people, and (g) combinations thereof in their making of determinations regarding points where selected measure points will be located on sensor observation-derived representations, and wherein at least one member selected from the group consisting of the (a) tools, (b) methodologies, (c) programming, (d) data, (e) information, (f) people, and (g) combinations thereof are utilized for making at least one type of determination selected from the group consisting of:

(i) determinations of where selected measure points will be located on sensor observation-derived representations of specific aspects, characteristics, or features of any one specific person who is a subject of sensor observations, (ii) determinations of where selected measure points will be located on sensor observation-derived representations of specific aspects, characteristics, or features of people who are sensor observations subjects that are members of specific groups of people, and (iii) determinations of where selected measure points will be located on sensor observation-derived representations of specific aspects, characteristics, or features of people who are sensor observation subjects from a complete spectrum of people who are sensor observation subjects.

In some embodiments of the universal health metrics monitors, analytically rich aspects, characteristics, or features of people who are subjects of sensor observations include aspects, characteristics, or features from a complete spectrum of sensor-observable analytically rich aspects, characteristics, or features of people;
- wherein measure points are utilizable in locating selected analytically rich aspects, characteristics, or features of or from sensor observation-derived representations of people;
- wherein measure points are utilizable for purposes from a complete spectrum of purposes for which measure points that are utilized in locating selected analytically rich aspects, characteristics, or features of or from sensor observation-derived representations of people can be utilized;
- the spectrum of analytically rich aspects, characteristics, or features of or from sensor observation-derived representations of people includes sensor observation-derived representations of (a) scars, (b) marks, (c) wounds, (d) fingerprint features, (e) axis points at joints, (f) tips of noses, (g) corners of eyes, (h) centers of pupils, (i) corners of mouths, (j) tips of fingers, (k) patterns of sweat glands, (l) coughs, (m) tremors, (n) shivers, (o) voices, (p) pulses, (q) blood pressure, (r) blood oxygen saturation, (s) respiration, or (t) any other analytically rich aspects, characteristics, or features of or from sensor observation-derived representations of people.

In some embodiments, universal health metrics monitors are further configurable for making selected determinations regarding or utilizing sensor observations or people who are the subjects of sensor observations; wherein the sensor observations are made: (a) at points in time or (b) over periods of time, and the universal health metrics monitors include, in datasets, informational representations regarding or utilizing selected analytically rich changes that occur over time to sensor-observable aspects, characteristics, or features of or from sensor observation-derived representations of the subjects of the sensor observations.

In some embodiments, universal health metrics monitors are further configurable for utilizing analytically rich changes that occur over time to people who are subjects of sensor observations; these changes include changes to aspects, characteristics, or features of sensor observation-derived representations of people's (a) heads, (b) faces, (c) mouths, (d) eyes, (e) eyebrows, (f) noses, (g) arms, (h) hands, (i) fingers, (j) legs, (k) feet, (l) necks, (m) torsos, (n) skin, (o) hearts, (p) stomachs, (q) intestines, (r) livers, (s) kidneys, (t) lungs, (u) breath, (v) vascular systems, (w) brains, (x) spinal cords, (y) neural systems, (z) neural activities, (aa) digestive systems, (bb) digestive activities, (cc) skeletons, (dd) blood, (ee) odors, (ff) voices, (gg) movements, (hh) tips of noses, (ii) corners of eyes, (jj) centers of pupils, (kk) axis points at joints, (ll) patterns of blood oxygenation during respiration cycles, (mm) presence of chemicals, compounds, or odors, or (nn) aspects, characteristics, or features of sensor observation-derived representations of people from a complete spectrum of other aspects, characteristics, or features of sensor observation-derived representations of people where sensor-observable analytically rich changes occur over time.

In some embodiments, universal health metrics monitors are further configurable for making selected determinations that are utilized in processes of accurately or reliably granting or denying people or cyber devices access to at least one member selected from the group consisting of (a) all or parts of universal health metrics monitors or bicorders, (b) all or parts of resources that are being utilized by universal health metrics monitors or bicorders, and (c) all or parts of resources that are utilizing universal health metrics monitors or bicorders The universal health metrics monitors, wherein selected determinations include determinations of any indicated measures of probability that exist of one specific yet-to-be-identified person being the same person as one specific known person; wherein these measures of probability range from making determinations that one specific yet-to-be-identified person absolutely is not one specific known person; through making determinations of any intermediate indicated measure of probability that exist of the one specific yet-to-be-identified person being the one specific known person; to making determinations that the one specific yet-to-be-identified person absolutely is the one specific known person.

In some embodiments, universal health metrics monitors are further configurable for being utilized for accurately or reliably performing testing of identities of specific people; wherein universal health metrics monitors' identity testing can be configured to utilize selected levels of participation by people who are subjects of the identity testing; and wherein the selected levels of participation range from tested people being observable by sensors, but not consciously engaged in the testing; to the tested people being observable and consciously engaged participants in the testing.

In some embodiments, universal health metrics monitors are configurable for being utilized for making selected one-time single-event test determinations regarding or utilizing selected sensor-observed analytically rich aspects, characteristics, or features of people's health;
- the selected one-time single-event test determinations are configurable for being made or utilized in real time or at times thereafter;
- the selected one-time single-event test determinations are made utilizing data from a complete spectrum of data that can be utilized by the universal health metrics monitors in their making of one-time single-event test determinations regarding or utilizing selected sensor-observed analytically rich aspects, characteristics, or features of people's health;
- selected analytically rich aspects, characteristics, or features of people's health are from a complete spectrum of sensor-observable analytically rich aspects, characteristics, or features of people's health;
- a complete spectrum of test determinations regarding or utilizing selected sensor-observable analytically rich aspects, characteristics, or features of people's health includes test determinations regarding the presence of (a) COVID-19, (b) H1N1, (c) Ebola, (d) cancer, or (e) a complete spectrum of other aspects, characteristics, or features of people's health that can be sensor-observed, tested, and accurately or reliably reported on;
- the one-time single-event test determinations regarding or utilizing selected sensor-observed analytically rich aspects, characteristics, or features of people's health can be utilized for purposes from a complete spectrum of purposes for which one-time single-event test determinations regarding or utilizing sensor-observed analytically rich aspects, characteristics, or features of people's health can be utilized;

the complete spectrum of purposes for which the one-time single-event test determinations can be utilized includes making test determinations regarding or utilizing sensor-observed analytically rich aspects, characteristics, or features of people's health prior to or immediately prior to tested people being granted or denied access to at least one member selected from a group consisting of (i) schools, (ii) public transportation, (iii) houses of worship, (iv) workplaces, (v) events, (vi) sporting activities, (vii) restaurants, (viii) bars, (ix) stores, (x) hospitals, (xi) parks, (xii) prisons, (xiii) nursing homes, (xiv) grocery stores, (xv) theaters, (xvi) gyms, (xvii) health care providers' offices, (xviii) concerts, (xix) salons, (xx) meat processing plants, and (xxi) other places or activities where it is required or desired to determine if tested people do or do not have selected aspects, characteristics, or features of their health that would or should exclude specific tested people from gaining access to those places or activities.

In some embodiments, universal health metrics monitors are further configurable for utilizing measure points in their locating of sensor observation-derived representations of selected analytically rich aspects, characteristics, or features of or from sensor observation-derived representations of people's faces;
the measure points are utilized for purposes from a complete spectrum of purposes for which measure points that are utilized in the locating of analytically rich aspects, characteristics, or features of or from sensor observation-derived representations of people's faces of can be utilized;
the complete spectrum of purposes for which measure points that are used in locating selected analytically rich aspects, characteristics or features of or from sensor observation-derived representations of people's faces can be utilized includes (a) determining identities of yet-to-be-identified people, (b) authenticating claimed identities of yet-to-be-identified people, (c) determining people's facial affects, (d) determining people's facial expressions, (e) determining gaze of people's eyes, (f) determining sensor or camera angles, (g) determining sensor observation lighting circumstances, (h) determining people's poses, (i) determining what portions of people's faces are being observed, (j) determining measures of people's state of mental or physical health, (k) determining people's pulse rates, (l) determining people's blood pressure, (m) determining relationships between sensors and measure points that are located on sensor observation-derived representations of people's faces, (n) identifying occurrences of micro-expressions, and (o) making determinations from a complete spectrum of other determinations for which measure points used in locating selected analytically rich aspects, characteristics, or features of or from sensor observation-derived representations of people's faces can be utilized.

In some embodiments, universal health metrics monitors are further configurable for making selected determinations regarding or utilizing differences between sensor observation-derived representations that are captured at an exact time that increased blood flow from a heartbeat is at its highest level, and sensor observation-derived representations that are captured at a lower level of blood flow, including the lowest level of blood flow; the changes can be used for making determinations regarding a person's health that cannot be made using only one of the sensor observation-derived representations;
wherein the determinations are from a complete spectrum of health determinations that can be made regarding or utilizing differences between sensor observation-derived representations that are captured at the time that increased blood flow from a heartbeat is at its highest level, and sensor observation-derived representations that are captured at a lower level of blood flow, including the lowest level of blood flow.

In some embodiments, universal health metrics monitors are further configured for making selected determinations regarding or utilizing measured locations of or measured orientations of selected analytically rich aspects, characteristics, or features of or from sensor observation-derived representations of people;
the analytically rich aspects, characteristics, or features of or from the people are from a complete spectrum of sensor observation-derived representations of analytically rich aspects, characteristics, or features of or from people;
measured locations of or measured orientations of the selected analytically rich aspects, characteristics, or features of or from the sensor observation-derived representations of the people include, for example, measured locations of or measured orientations of (a) sensor observation-derived representations of micro-expressions on sensor observation-derived representation of people's faces, (b) sensor observation-derived representations of external wounds on sensor observation-derived representations of people, (c) sensor observation-derived representations of orientations of people's joints on sensor observation-derived representations of people, (d) sensor observation-derived representations of skin irregularities on sensor observation-derived representations of people, (e) sensor observation-derived representations of axis points at joints on sensor observation-derived representations of people, (f) sensor observation-derived representations of pulse points on sensor observation-derived representations of people, or (g) sensor observation-derived representations of analytically rich aspects, characteristics, or features of people from a complete spectrum of other sensor observation-derived representations of analytically rich aspects, characteristics, or features of people.

In some embodiments, universal health metrics monitors are further configurable for utilizing measure points in their locating of sensor observation-derived representations of one or more tips of people's fingers;
the measure points are utilized for purposes from a complete spectrum of purposes for which measure points that are utilized in locating sensor observation-derived representations of people's fingertips can be used;
the complete spectrum of purposes includes utilization of the measure points as components of fingertip-to-cyber device touchless user interfaces; and
the cyber devices are types of cyber devices from a complete spectrum of types of cyber devices that can utilize fingertip-to-cyber device touchless user interfaces.

In some embodiments, universal health metrics monitors are further configurable for utilizing measure points in their locating of axis points from sensor observation-derived representations of joints of people;
the measure points that locate the axis points are utilized for purposes from a complete spectrum of purposes for which measure points that locate sensor observation-derived representations of axis points of people's joints can be utilized; and the complete spectrum of purposes for which measure points that are utilized in locating sensor observation-derived representations of axis points of joints of people can be utilized includes (a) making selected determinations regarding or utilizing observed geometries of sensor observation-derived representation of joints of people, or (b) making selected determinations that utilize measure points that locate sensor observation-derived representations of axis points of joints of people for purposes from a complete spectrum of other purposes for which measure points that locate sensor observation-derived representations of axis points of joints of people can be utilized.

In some embodiments, universal health metrics monitors are further configured to be utilized for making selected determinations regarding or utilizing analytically rich aspects, characteristics, or features of observed geometries of sensor observation-derived representation of joints of people; and the selected analytically rich aspects, characteristics, or features of geometries of the sensor observation-derived representations of joints of people are utilized for purposes from a complete spectrum of purposes for which analytically rich aspects, characteristics, or features of observed geometries of sensor observation-derived representations of joints of people can be utilized.

In some embodiments, universal health metrics monitors use measure points in their making of selected measurements;

the selected measurements are from a complete spectrum of measurements that can be made through use of measure points that are utilized in locating selected analytically rich aspects, characteristics, or features of or from sensor observation-derived representations; and the complete spectrum of measurements that can be made through use of the measures point includes (a) measured distances between measure points, (b) measured angles where lines between measure points meet or intersect, (c) measured locations of measure points, aspects, characteristics, or features, (d) measured orientations of measure points, aspects, characteristics, or features, (e) measured relationships between measure points, aspects, characteristics, or features, (f) time of capture of sensor observations or parts thereof, (g) measured pressures at or in areas of measure points, (h) measured temperatures at or in areas of measure points, (i) measured levels of colored light at or in areas of measure points, (j) measured grayscale levels at or in areas of measure points, (k) measured odors at or in areas of measure points, (l) measured chemical presences at or in areas of measure points, (m) measured sound at or in areas of measure points, or (p) measures of sensor-observable analytically rich aspects, characteristics, or features from a complete spectrum of other measurable sensor-observable analytically rich aspects, characteristics, or features of or from sensor observation-derived representations that can be located or reported on through utilization of measure points.

In some embodiments, universal health metrics monitors or bicorders are configurable for performing their operations, or parts thereof, in any usable order or sequence.

In some embodiments, universal health metrics monitors are further configurable for achieving selected attainable level of accuracy goals for selected determinations and the attainable level of accuracy goals falls in a range extending from 0% accuracy, and goes up to and includes 100% accuracy.

In some embodiments, universal health metrics monitors are further configurable for utilizing information or informational representations from sources that are not first-series observation operations or second-series observation operations.

In some embodiments, universal health metrics monitors or bicorders are further configurable for manipulating in possible ways operations of universal health metrics monitors, bicorders-utilized resources, or operations of the universal health metrics monitors or bicorders; the manipulating provides the universal health metrics monitors or bicorders with selections of possible utilizations; the manipulating is utilized for purposes from a complete spectrum of purposes for which the manipulating can be utilized; the complete spectrum of purposes for utilizing the manipulating includes a purpose of aiding universal health metrics monitors or bicorders in their operations or the making of selected health determinations.

In some embodiments, universal health metrics monitors, all or part of sensor observation datasets from sources that are not first-series observation operations are included as all or part of first-series observation datasets; and all or part of sensor observation datasets from sources that are not second-series observation operations are included as all or part of second-series observation datasets.

In some embodiments, universal health metrics monitors are further configured to include health metrics monitor history; wherein the health metrics monitor history is comprised of health metrics monitor history records; and the health metrics monitor history records are utilizable for purposes from a complete spectrum of purposes for which health metrics monitor history records can be utilized.

The present disclosure further pertains to universal health metrics monitors; the universal health metrics monitors comprise or utilize tools, methodologies, programming, computers, sensor data, bicorders, and other necessary resources, all of which are utilized in capturing, selecting, deriving, or utilizing data for or from concise datasets; the universal health metrics monitors are configurable for using data for or from concise datasets in their making of selected determinations regarding or utilizing sensor observations or the health of people who are sensor observation subjects; the universal health metrics monitors further comprise deriving or utilizing information from points in time or from periods of time, from a complete spectrum of information that includes information regarding observed analytically rich aspects, characteristics, or features of or from sensor observations or people who are subjects of sensor observations, thereby obtaining sensor-derived information;

the sensor observations are types of sensor observation from a group consisting of (a) visual sensor observations, (b) audible sensor observations, (c) thermal sensor observations, (d) olfactory sensor observations, (e) tactile sensor observations, (f) chemical sensor observations, or (g) types of sensor observations, from a complete spectrum of other types of sensor observations that can be utilized by universal health metrics monitors;

the universal health metrics monitors capture, select, derive, or utilize data for or from datasets, or make selected health determinations through utilization of (a)

tools, (b) methodologies, (c) programming, (d) computers, (e) bicorders, (f) sensor data, (g) information, (h) criteria that are utilized by universal health metrics monitors, and (i) other necessary resources;

the universal health metrics monitors make at least one type of health determination selected from the group consisting of (i) one-time, single event health determinations, (ii) intermittently made health determinations, and (iii) constantly made health determinations;

the selected health determinations are utilized for purposes from a complete spectrum of purposes for which health determinations regarding or utilizing sensor observations or people who are subjects of sensor observations can be utilized; and the universal health metrics monitors further comprise utilizing at least one part of at least one operation selected from a group consisting of (a) First-series observation operations, wherein universal health metrics monitors utilize sensor observations; wherein the sensor observations or people who are subjects of the sensor observations have previously determined aspects, characteristics, or features; the universal health metrics monitors recognize the aspects, characteristics, or features; the recognized aspects, characteristics, or features are utilizable by the universal health metrics monitors in their making of selected health determinations; the universal health metrics monitors assign appropriate informational representations regarding selected known aspects, characteristics, or features of the sensor observations or the people who are subjects of the sensor observations; the universal health metrics monitors include all or parts of the informational representations in first-series observation datasets, (b) Second-series observation operations, wherein universal health metrics monitors utilize sensor observations; and wherein the sensor observations or people who are subjects of the sensor observations have selected yet-to-be-determined aspects, characteristics, or features; the universal health metrics monitors recognize the selected yet-to-be-determined aspects, characteristics, or features; the universal health metrics monitors assign appropriate informational representations regarding any selected and now determined aspects, characteristics, or features of the sensor observations or the people who are subjects of the sensor observations; the universal health metrics monitors include all or parts of the informational representations in second-series observation datasets, (c) measure point operations, wherein universal health metrics monitors utilize measure points in their locating of selected analytically rich aspects, characteristics, or features of or from sensor observation-derived representations of sensor observations or people who are subjects of sensor observations; the universal health metrics monitors assign appropriate informational representations regarding the measure points, aspects, characteristics, or features of or from the sensor observation-derived representations; wherein all or parts of the informational representations are stored or utilized by universal health metrics monitors in their making of selected health determinations regarding or utilizing the sensor observations or the people who are subjects of the sensor observations, (d) concise datasets operations, wherein universal health metrics monitors utilize concise datasets in their making of selected health determinations; the concise datasets include selected sensor data or derived data; wherein the selected sensor data comprises informational representation that were selected from sensor observation datasets; and the derived data comprises informational representations that were derived from (i) processing selected informational representations from sensor observation datasets, or (ii) processing selected informational representations from derived data; the informational representations from the selected sensor data or the informational representations from the derived data are utilizable by the universal health metrics monitors in their making of selected health determinations regarding or utilizing sensor observations or people who are subjects of sensor observations; and the derived data are derived utilizing tools, methodologies, or programming from a complete spectrum of tools, methodologies, or programming that can be utilized in deriving informational representations from sensor data, or from or for derived data, (e) matching operations, wherein universal health metrics monitors' matching operations include matching informational representation from second-series observation datasets to comparable informational representation from first-series observation datasets, (f) comparing operations, wherein universal health metrics monitors comparing operations include comparing informational representation from second-series observation datasets to comparable informational representation from first-series observation datasets and providing conclusions or determinations from the comparing, (g) determining operations, wherein universal health metrics monitors utilize conclusions or determinations from comparing operations, or information in their making of selected health determinations, and (h) reporting operations, wherein universal health metrics monitors include reporting operations, wherein universal health metrics monitors provide selected reports regarding or utilizing selected aspects, characteristics, or features of or from all or parts of cycles of utilization of the universal health metrics monitors.

DETAILED DESCRIPTION

Figure 1:
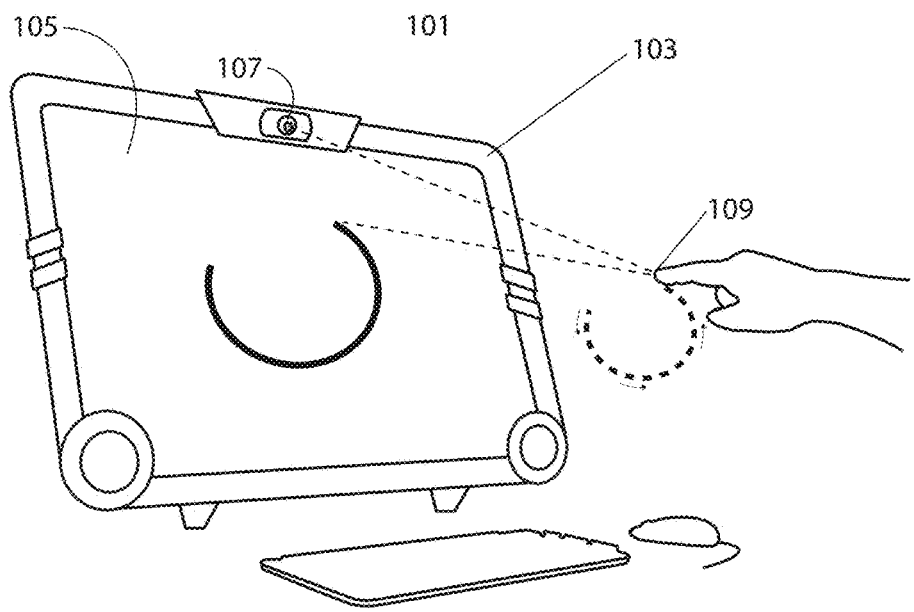
FIG. 1 is an illustration of a particular non-limiting embodiment of utilization of a touchless user interface of a desktop configured universal health metrics monitor in accordance with the teachings herein.

The present disclosure pertains to scalable, configurable, complete spectrum, universal health metrics monitors that are configurable for making selected determinations regarding people's health. Universal health metrics monitors' resources include computing devices, tools, methodologies, programming, data, information, selected criteria, and other necessary resources that are utilized by the universal health metrics monitors in their making of selected determinations regarding people's health. The selected determinations are from a complete spectrum of sensor data-enabled determinations that can be made regarding people's health.

Universal health metrics monitors are configurable for making selected determinations regarding or utilizing measure points. These determinations are used in the locating of selected analytically rich aspects, characteristics, or features of or from sensor observation-derived representations.

Universal health metrics monitors are configurable for assigning or utilizing informational representations regarding or utilizing measure points or analytically rich aspects, characteristics, or features of or from sensor observation-derived representations.

Additionally, universal health metrics monitors are configurable for utilizing concise datasets in their making of selected determinations.

Unless otherwise specified herein, each of the following will apply throughout this entire disclosure:

(a) universal health metrics monitors are scalable and therefore they can be scaled to include universal health metrics monitor resources from any point in a range of included or utilized universal health metrics monitor resources, wherein at one end of the range universal health metrics monitors are scaled to include or utilize the fewest universal health metrics monitor resources, and at the other end of the range universal health metrics monitors are scaled to include or utilize all universal health metrics monitor resources;

(b) universal health metrics monitors are configurable and they can be configured to be utilized in one or more configurations;

(c) universal health metrics monitors or parts thereof are configurable for universal utilization;

(d) universal health metrics monitors are configurable for providing selections of criteria, wherein criteria are selected from a complete spectrum of criteria that are utilizable by universal health metrics monitors in their making of selected determinations regarding or utilizing sensor observations or sensor observation subjects;

(e) universal health metrics monitors are complete spectrum health metrics monitors and they are configurable for utilizing health metrics monitor resources from the complete spectrum of utilizable universal health metrics monitor resources in their making of selected cyber determinations regarding or utilizing sensor observations or the health of people who are subjects of sensor observations from a complete spectrum of sensor observations or people who are subjects of sensor observations. Further, universal health metrics monitors are configurable for providing for determination needs from a complete spectrum of needs for determinations regarding or utilizing sensor observations or the health of people who are subjects of sensor observations; and (f) an operational goal of universal health metrics monitors is to preferably utilize best performing blends of as simple, concise, and efficient operations as possible.

Universal health metrics monitors are configurable for making selected health determinations regarding or utilizing sensor observations or sensor observation subjects from a complete spectrum of sensor observations or people who are subjects of sensor observations.

Definitions

In the present disclosure, the following terms or phrases have the meanings indicated below.

Adjusting factors: tools, methodologies, programming, or combinations thereof that are utilized to enable universal health metrics monitors to accurately or reliably make selected determinations when there are observation circumstances or analytically rich aspects, characteristics, or features of or from second-series observations or second-series observation subjects that are not exact matches to the observation circumstances or analytically rich aspects, characteristics, or features of or from the first-series observations or the first-series observation subjects to which they are being matched or compared.

Analytically rich: being usable by universal health metrics monitors in their accurate or reliable making of selected determinations.

Aspects: one or more aspects, characteristics, or features of or from sensor observation-derived representations of sensor observations or sensor observation subjects.

Aspects, characteristics, or features: at least one member selected from the group consisting of (a) aspects, (b) characteristics, or (c) features of or from sensor observation-derived representations of sensor observations or sensor observation subjects.

Behavioral analysis: analysis of sensor-observed behavior of organisms or devices.

Bicorders: physical devices or virtual devices that are configured to capture or record all or selected parts of sensor observations of analytically rich aspects, characteristics, or features of people's health.

Biological characteristics: biological aspects, characteristics, or features of biological organisms, including people, that are sensor-observable.

Cameras: image sensors; video-formatted image sensors.

Capture/capturing: the use of cyber resources for acquiring or recording cyber sensor observations.

Characteristics: one or more aspects, characteristics, or features of or from sensor observation-derived representations of sensor observations or sensor observation subjects.

Complete spectrum: the complete set of possible choices for a given variable or option, which includes the subset of available choices for any given variable or option; thus, for example, the complete spectrum of cyber resources is the complete set of possible cyber resources, which includes all available cyber resources.

Concise: including or utilizing little or no unnecessary data.

Concise datasets: small datasets; datasets that contain little or no unnecessary data; datasets that are typically at least 90% smaller than the original sensor observation datasets from which they were selected or derived; datasets that are comprised of selected analytically rich sensor observation data or analytically rich derived data.

Constant determinations: cyber determinations that are made at any frequency that essentially results in the uninterrupted continuous making of the cyber determinations.

Criteria: a group of selectable options that contains one or more members.

Cyber: utilizing non-biological processing of programming, the term includes anything (such as, for example, devices, tools, methodologies, programming; or files) that utilizes, or is utilized for non-biological processing of programming.

Derived data: data that are derived from the processing of selected sensor data or selected derived data.

Determinations: one or more questions that are answered through utilization of cyber resources.

Determinations of identity: cyber determinations of previously unknown identity or cyber determinations for authenticating or verifying claimed identity.

Features: one or more aspects, characteristics, or features of or from sensor observation-derived representations of sensor observations or sensor observation subjects.

From: from; selected from.

Indicators: analytically rich aspects, characteristics, or features of or from sensor observation-derived representations that are assigned appropriate informational representations that are utilizable in the making of selected cyber determinations.

Informational representations: data; designations, names, labels, or measurements that are appropriately assigned to sensor-observed analytically rich aspects, characteristics, or features of or from sensor observation-derived representations of sensor observations or sensor observation subjects.

Measure points: points or pointers that are utilized in the locating of selected analytically rich aspects, characteristics, or features of or from sensor observation-derived representations; measure points are utilized to provide reproducible structures from which (a) measurements are made, (b) structured analysis is performed on sensor observation-derived representations of sensor observations or sensor observation subjects, or (c) sensor observation-derived representations from multiple sensors or from multiple times of capture can reliably be aligned.

Monitoring: analysis of current, recent, or past sensor data for the purpose of identifying selected aspects, characteristics, or features of or from sensor observation-derived representations of people's health.

Observation/observations: one or more sensor observations.

One time/one-time: occurring at only one specific point in time or occurring over only one specific short period of time.

Points: the smallest addressable locations from sensor observation-derived representations.

Physical analysis: analysis of sensor-observable physical aspects, characteristics, or features of sensor observation subjects.

Physiological analysis: analysis of sensor-observable physiological aspects, characteristics, or features of sensor observation subjects.

Real time/real-time: occurring at essentially the exact moment in time that a sensor observation is captured; occurring at a time that was so close to the time when a sensor observation was captured that people would not notice latency.

Recognized: analytically rich aspects, characteristics, or features of or from sensor observation-derived representations that are accurately or reliably identified.

Selected determinations: selected cyber determinations regarding or utilizing sensor observations or sensor observation subjects.

Series: groups of one or more.

Smudges: sensor-observed artifacts of prior light that were fully present at previous points in time; artifacts of prior light that are recognizable parts of sensor observation-derived representations; prior light from previous points in time (possibly in increments of 500 points in time or more per second) that can still be captured by sensors for one or more points in time past the final point in time when the sensor-observed representation of the fully present light was captured; artifacts of light that can be utilized in making selected cyber determinations regarding or utilizing what occurred at one or more points in time prior to when images were captured or recorded; artifacts of light that can be utilized in the making of selected cyber predictions of what might be observed in the future; reflected or refracted light that alters the observed levels of colored light at pixels that adjoin or that are in the areas of the refracted or the reflected light.

Smudge analysis: analysis of smudges from sensor observation-derived representations.

Spectrum: a complete spectrum; a complete set of possible choices for a given variable or option.

Tells: analytically rich aspects, characteristics, or features of or from sensor observation-derived representations that are utilizable by universal health metrics monitors in their accurate or reliable making of one or more selected health determinations.

Universal health metrics monitors: one or more scalable, configurable, complete spectrum universal health metrics monitors.

Unique biological aspects, characteristics, or features: any single sensor-observable aspect, characteristic, or feature of a biological organism, or any combination of sensor-observable aspects, characteristics, or features of one biological organism (e.g., a biological fingerprint) that are considered to be unique to the one specific observed biological organism.

Visual analysis: the analysis of images from image sensor observation-derived representations.

X: designation for horizontal lines from pixel grids.

Y: designation for vertical lines from pixel grids.

Yet-to-be-identified person: one specific person who is a subject of a second-series observation; one specific person who has not yet been determined to be the same person as one specific known person.

Universal Health Metrics Monitors

The disclosed universal health metrics monitors are configurable for filling unanswered needs that presently exist with prior art—unanswered needs for a complete spectrum of reliable sensor observation-derived determinations regarding the health of people who are subjects of sensor observations. A few features of universal health metrics monitors are as follow (a) constantly making selected cyber determinations regarding whether or not one specific known person and one specific yet-to-be-identified person are the same person at any selected attainable level of accuracy, including 100% accuracy;

(b) utilizing any necessary number of analytically rich aspects, characteristics, or features of or from one specific known person, or one specific yet-to-be-identified person, in the making of determinations regarding the identity of the one specific yet-to-be-identified person;

(c) the making of at least one member selected from the group consisting of (i) one-time, single-event cyber determinations regarding the health of a person, (ii) intermittently provided cyber determinations regarding the health of a person, or (iii) constantly provided cyber determinations regarding the health of a person who is a subject of sensor observations;

(d) utilizing informational representations regarding sensor observations or sensor observation subjects in the making of selected determinations regarding the health of a person who is a subject of sensor observations;

(e) utilizing measure points in the locating of selected analytically rich aspects, characteristics, or features of or from sensor observation-derived representations in the making of selected determinations regarding the health of a person who is a subject of sensor observations;

(f) providing or utilizing standard tools, methodologies, programming, processes, procedures, measurements, designations, informational representations, names, or definitions for accurately or reliably representing any aspects, characteristics, or features of universal health metrics monitors or their operations;

(g) enabling absolute security or privacy for information or resources that are utilized by universal health metrics monitors or that are utilizing universal health metrics monitors;

(h) utilizing selected criteria for observing, recognizing, locating measure points, assigning appropriate informational representations, storing data, measuring, matching, comparing, determining, reporting, or any other operations of universal health metrics monitors;

(i) making selected determinations utilizing observations that were not captured utilizing universal health metrics monitors or bicorders;

(j) utilizing useful information that was derived from sensor observations in the making of selected determinations regarding the health of a person who is a subject of sensor observations;

(k) utilizing useful information of any type from any source in the making of selected determinations regarding the health of a person who is a subject of sensor observations;

(l) utilizing appropriately assigned standard informational representations regarding or utilizing measure points or defined points or areas of sensor observation-derived representations that are located through the utilization of measure points; or (m) utilizing appropriately assigned informational representations regarding sensor observations or sensor observation subjects in the making of selected determinations regarding the health of a person who is a subject of sensor observations.

The following list includes a portion of the resources, features, or services from a complete spectrum of resources, features, or services that universal health metrics monitors are configurable for providing, including, or utilizing:

(a) health determinations utilizing sensor observations from a complete spectrum of sensor observation-derived health determinations;

(b) health determinations regarding or utilizing some or all analytically rich aspects, characteristics, or features of or from sensor observation-derived representations of a person's health from a complete spectrum of analytically rich aspects, characteristics, or features of or from sensor observation-derived representations of people's health;

(c) health determinations that fill some or all needs from a complete spectrum of needs for health determinations that utilize sensor observations of people;

(d) health determinations regarding or utilizing sensor observations or sensor observation subjects that are made at one or more selected attainable levels of accuracy, which can include 100% accuracy;

(e) health determinations that utilize some or all resources from a complete spectrum of resources that are utilizable in the making of the selected health determinations;

(f) health determinations regarding or utilizing sensor observations or sensor observation subjects that utilize information from a complete spectrum of useful information;

(g) health determinations that utilize some or all sensor observations from a complete spectrum of sensor observations;

(h) health determinations regarding or utilizing sensor observations or people who are sensor observation subjects that provide for selection of some or all criteria from a complete spectrum of useful criteria;

(i) health determinations regarding or utilizing sensor observations or sensor observation subjects, wherein universal health metrics monitors utilize (i) standard processes, (ii) standard procedures, (iii) standard informational representations, or (iv) standard definitions for accurately or reliably representing any analytically rich aspects, characteristics, or features of or from operations of universal health metrics monitors;

(j) health determinations regarding or utilizing sensor observations or sensor observation subjects that are made (i) as one-time events, (ii) intermittently, or (iii) constantly;

(k) testing of identity prior to granting or denying people or cyber devices initial or continued access to (i) universal health metrics monitors, (ii) cyber resources that are being utilized by universal health metrics monitors, or (iii) cyber resources that are utilizing universal health metrics monitors;

(l) security or privacy, which can include absolute security or privacy for some or all cyber resources or activities that are utilizing or that are being utilized by universal health metrics monitors;

(m) utilization of sensor observations of any one specific person in the making of selected cyber determinations regarding the identity of the one specific person, wherein the one specific person, who is a subject of sensor observations is at any point in a range of from being in the presence of sensors, but not being consciously engaged in determination of identity observations, to being in the observable presence of sensors and being consciously engaged in determination of identity sensor observations;

(n) scalability of included or utilized universal health metrics monitors resources, wherein universal health metrics monitors are configurable for including or utilizing only the resources that are necessary to include or utilize for the making of selected health determinations at any point in a range; wherein at the smallest end of the range, universal health metrics monitors are configurable for providing for the smallest of all health determination needs for included or utilized universal health metrics monitor resources, and at the largest end of the range, universal health metrics monitors are configurable for including or utilizing all universal health metrics monitor resources;

(o) ease of use in any or all phases of operations of universal health metrics monitors;

(p) persistence when attempting to achieve selected goals or any parts thereof;

(q) utilization of observed physical, visual, behavioral, physiological, or biological analytically rich aspects, characteristics, or features of or from sensor observation-derived representations of people when making selected health determinations regarding people;

(r) alteration of the operations of universal health metrics monitors or any resources that are being utilized by universal health metrics monitors; these alterations are made for any useful purpose which includes aiding in making selected health determinations;

(s) utilization of useful information that was derived from any source;

(t) appropriately assigning informational representations regarding or utilizing measure points from sensor observation-derived representations;

(u) utilization of unique combinations of analytically rich aspects, characteristics, or features of or from sensor observation-derived representations;

(v) utilization of changes that occur over time to analytically rich aspects, characteristics, or features of or from sensor observation-derived representations;

(w) utilization of combinations of observed analytically rich aspects, characteristics, or features of or from sensor observation-derived representations of sensor observations or people who are sensor observation subjects that were observed over periods of time or at points in time;

(x) utilization of useful sensor observation data or useful information from any source;

(y) determining or utilizing levels of health determination accuracy that have been achieved;

(z) determining or utilizing measures of adequacy of available resources;

(aa) utilizing universal health metrics monitors' resources for capturing first-series observations or second-series observations; or (bb) storing informational representations regarding measure points or analytically rich aspects, characteristics, or features of or from sensor observation-derived representations in datasets, wherein the stored data can be utilized in real time or thereafter in the making of selected health determinations.

At present we live in a technologically interconnected world where the vast spectrum of available cyber resources is ever widening. Over time, our world appears to be destined to provide every possible cyber resource that humanity could ever want or need. Included in those resources and in accordance with the teachings herein will be scalable, configurable, complete spectrum universal health metrics monitors that utilize measure points from sensor observation-derived representations or datasets in their making of selected determinations regarding or utilizing sensor observations or people who are sensor observation subjects.

Universal health metrics monitors are configurable for utilizing at least one member selected from the group consisting of:

(a) tools, methodologies, or programming for selecting the analytically rich aspects, characteristics, or features of or from sensor observation-derived representations that will be utilized in the making of selected health determinations;

(b) tools, methodologies, or programming for identifying the analytically rich aspects, characteristics, or features of or from sensor observation-derived representations that will be located through utilization of measure points;

(c) tools, methodologies, or programming for determining the measure points that will be included as members of standard target sets of measure points, wherein standard target sets of measure points can be configured to be utilized in the making of selected health determinations regarding or utilizing selected sensor observations of people under specific sets of or under varying sets of sensor observation circumstances;

(d) tools, methodologies, or programming for accurately or reliably utilizing measure points in the locating of selected analytically rich aspects, characteristics, or features of or from sensor observation-derived representations of people;

(e) tools, methodologies, or programming for assigning appropriate informational representations regarding or utilizing at least one member selected from the group consisting of (i) measure points, (ii) analytically rich aspects, characteristics, or features, (iii) sensor observations, or (iv) sensor observation subjects;

(f) tools, methodologies, or programming for storing informational representations regarding or utilizing at least one member selected from the group consisting of (i) measure points, (ii) analytically rich aspects, characteristics, or features, (iii) sensor observations, or (iv) sensor observation subjects;

(g) tools, methodologies, or programming for appropriately assigning or utilizing standard informational representations regarding at least one member selected from the group consisting of (i) measure points, (ii) analytically rich aspects, characteristics, or features, (iii) sensor observations, or (iv) sensor observation subjects, in the making of selected health determinations; or (h) any other tools, methodologies, or programming that can be utilized by universal health metrics monitors in their making of selected health determinations regarding or utilizing sensor observations or the health of people who are sensor observation subjects.

The disclosed universal health metrics monitors are configurable for making any health determinations regarding or utilizing sensor observations or sensor observation subjects that our world could ever want or need. A further discussion of this universal concept is disclosed in:

(a) co-pending U.S. patent application Ser. No. 16/998,868 (Aronson), filed Aug. 20, 2020, entitled "Universal Operating System", having the same inventor, which is incorporated herein by reference in its entirety; which application is a continuation-in-part application of U.S. patent application Ser. No. 15/483,970 (Aronson), now abandoned, filed Apr. 10, 2017, entitled "Scalable Configurable Universal Operating System", having the same inventor, which is incorporated herein by reference in its entirety; which application is a continuation-in-part application of U.S. patent application Ser. No. 15/236,337 (Aronson), filed Aug. 12, 2016, issued as U.S. Pat. No. 9,660,996 on May 23, 2017, entitled "Point-of-Cyber-Access Cyber System", having the same inventor, which is incorporated herein by reference in its entirety; which application is a continuation-in-part application of U.S. patent application Ser. No. 14/447,283 (Aronson), filed on Jul. 30, 2014, issued as U.S. Pat. No. 9,479,507 on Oct. 25, 2016 (Aronson), entitled "Single-Point-of-Access Cyber System", having the same inventor, which is incorporated herein by reference in its entirety; which application is a continuation application of U.S. patent application Ser. No. 13/702,537 (Aronson), filed on Oct. 19, 2011, issued as U.S. Pat. No. 8,832,794 on Sep. 9, 2014, entitled "Single-Point-of-Access Cyber System", having the same inventor, which is incorporated herein by reference in its entirety; and (b) co-pending U.S. patent application Ser. No. 17/878,378 (Aronson), filed Aug. 1, 2022, entitled "Identity Authentication Process", now pending, having the same inventor, which is incorporated herein by reference in its entirety; which application is a continuation-in-part application of U.S. patent application Ser. No. 16/891,088 (Aronson), filed Jun. 3, 2020, issued as U.S. Pat. No. 11,444,947 on Sep. 13, 2022, entitled "Identity Testing Machine", having the same inventor, which is incorporated herein by reference in its entirety; which application is a continuation-in-part application of U.S. patent application Ser. No. 16/583,257 (Aronson), filed Sep. 26, 2019, issued as U.S. Pat. No. 10,708,271 on Jul. 7, 2020, entitled "Scalable Configurable Universal Full Spectrum Cyberspace Identity Verification Test", having the same inventor, which is incorporated herein by reference in its entirety; which application is a continuation-in-part application of U.S. patent application Ser. No. 15/456,542, (Aronson) filed Mar. 12, 2017, issued as U.S. Pat. No. 10,462,139 on Oct. 29, 2019, entitled "Scalable Universal Full Spectrum Cyber Determining Process", having the same inventor, which is incorporated herein by reference in its entirety; which application is a continuation-in-part application of U.S. patent application Ser. No. 15/071,075 (Aronson), filed Mar. 15, 2016, issued as U.S. Pat. No. 9,635,025 on Apr. 25, 2017 (Aronson), entitled "Scalable Universal Full Spectrum Cyber Determining Machine", having the same inventor, which is incorporated herein by reference in its entirety; which application is a continuation-in-part application of U.S. patent application Ser. No. 14/857,445 (Aronson), filed Sep. 17, 2015, issued as U.S. Pat. No. 9,319,414 on Apr. 19, 2016, entitled "Scalable Full Spectrum Cyber Determination Process", having the same inventor, which is incorporated herein by reference in its entirety; which application is a continuation-in-part application of U.S. patent application Ser. No. 14/316,196 (Aronson), filed Jun. 26, 2014, issued as U.S. Pat. No. 9,166,981 on Oct. 20, 2015, entitled "Full Spectrum Cyber Identification Determination Process", having the same inventor, which is incorporated herein by reference in its entirety; which application is a continuation of U.S. patent application Ser. No. 13/784,277 (Aronson), filed Mar. 4, 2013, issued as U.S. Pat. No. 8,769,649 on Jul. 1, 2014, entitled "Full Spectrum Cyber Identification Determination Process", having the same inventor, which is incorporated herein by reference in its entirety; which application is a continuation of U.S. patent application Ser. No. 13/688,925 (Aronson), filed Nov. 29, 2012, issued as U.S. Pat. No. 8,434,136 on Apr. 30, 2013, entitled "Full Spectrum Cyber Identification Determination Process", having the same inventor, which is incorporated herein by reference in its entirety.

As the spectrum of available cyber resources grows, so does the need for universal health metrics monitors that utilize concise, efficient, and accurate real-time tools, methodologies, programming, and sensor observation data in their accurate or reliable making of selected health determinations regarding or utilizing sensor observations or people who are subjects of sensor observations.

The more we rely on computing-based resources, the more those resources must be fully automated. In many cases, computing-based resources need to rely on automated real-time cyber determinations regarding occurrences in the physical world to make the best possible accurate and reliable cyber determinations. Universal health metrics monitors are configurable for utilizing best performing blends of as simple, concise, and efficient operations. Universal health metrics monitors are configurable for doing so, in part, through their utilization of measure points in the locating of selected analytically rich aspects, characteristics, or features of or from sensor-observation-derived representations of sensor observation or people who are sensor observation subjects. Use of measure points or target sets of measure points provides the structure that is needed for universal health metrics monitors to accurately or reliably make selected determinations regarding or utilizing sensor observations or the health of people who are sensor observation subjects.

Universal health metrics monitors are configurable to be at least one member selected from the group consisting of (a) single, self-contained universal health metrics monitors or bicorders, (b) universal health metrics monitors or bicorders that utilize or are utilized by interconnected resources, (c) universal health metrics monitors or bicorders that are utilized as integral or remote resources of other devices or systems, (d) universal health metrics monitors or bicorders that are virtual, physical, or combinations thereof, (e) universal health metrics monitors or bicorders that are stationary, mobile, or combinations thereof, (f) universal health metrics monitors or bicorders that are utilized by or utilize devices that are located in one or more locations, or (g) universal health metrics monitors or bicorders that are utilized by or utilize interconnected resources.

"Best performing" is preferably defined as the best possible performance or results that utilization of cyber devices, tools, methodologies, programming, or combinations thereof can achieve. Operations of universal health metrics monitors where best performing can be utilized as a preferred operational goal include (a) determining which analytically rich aspects, characteristics, or features of or from sensor observation-derived representations of people will be utilized to simply or efficiently provide selected determinations regarding a person's health, (b) determining the selections of points or areas of or from analytically rich aspects, characteristics, or features of or from sensor observation-derived representations that will be located through utilization of measure points, (c) capturing first or second-series sensor observations, (d) processing sensor observations, (e) locating selected measure points on sensor observation-derived representations, (f) assigning appropriate informational representations regarding or utilizing selected analytically rich aspects, characteristics, or features of or from sensor observation-derived representations, (g) providing structured storage of informational representations regarding or utilizing (i) sensor observations, (ii) subjects of sensor observations, or (iii) measure points; (h) utilizing measure points that are located on sensor observation-derived representations, (i) assigning or utilizing appropriate informational representations regarding or utilizing sensor observation-derived representations in the making of selected health determinations, (j) standardization of at least one member selected from the group consisting of (i) tools, (ii) methodologies, (iii) programming, (iv) selection of tools, methodologies, or programming to utilize, (v) processing of sensor observations, (vi) storing data, (vii) utilizing data, (viii) selecting of data from sensor observation datasets, (ix) deriving data, (x) assigning or utilizing definitions, (xi) making measurements, (xii) utilization of units of measure, (xiii) making adjustments for differences between first-series observations or observation circumstances and second-series observations or observation circumstances, (xix) making selected health determinations, (xx) aspects of the operations of universal health metrics monitors from a complete spectrum of other aspects of the operations of universal health metrics monitors, or (xxi) combinations thereof.

Universal health metrics monitors are configurable for the making of selected health determinations regarding or utilizing sensor observations or people who are subjects of sensor observations by means of matching or comparing informational representations regarding or utilizing yet-to-be-determined analytically rich aspects, characteristics, or features of or from second-series observations or second-series observation subjects to comparable informational representations regarding or utilizing known analytically rich aspects, characteristics, or features of or from first-series observations or first-series observation subjects.

Universal health metrics monitors are configurable for having the same outcomes occur every time the same observations are processed as part of first-series observation operations, or as part of second-series observation operations.

Universal health metrics monitors are configurable for utilizing standard processes or standard procedures to best achieve the goal of same reproducible outcomes from sensor observations of the same subject under differing sensor observation circumstances. As an example, a first-series observation is made of a person under a specific set of observation circumstances and standard tools, methodologies, and programming are utilized for assigning appropriate standard informational representations regarding or utilizing sensor observations of the person. When the same person is observed by a different sensor at a different time under a different set of observation circumstances, universal health metrics monitors are configurable for utilizing standard adjusting factors to compensate for the differences in sensor observation circumstances. Universal health metrics monitors use standard adjusting factors to aid in assigning the same standard informational representations to both sensor observations of the same person.

Operations of universal health metrics monitors where standard processes or standard procedures can be utilized in the making of selected health determinations include (a) determining which analytically rich aspects, characteristics, or features of or from sensor observation-derived representations will be located through utilization of measure points, (b) determining which standard target sets of measure points will be utilized for specific observation subjects or observation circumstances, (c) determining which measure points will be included in standard target sets of measure points, (d) determining the points on sensor observation-derived representations where selected measure points will be located, (e) appropriately assigning or utilizing standard informational representations regarding or utilizing analytically rich aspects, characteristics, or features of or from sensor observations or sensor observation subjects, (f) determining the sensors that were utilized in the making of sensor observations, (g) determining matches between informational representations from second-series observations and comparable informational representations from first-series observations, (h) deriving informational representations from the processing of first-series observation informational representations or second-series observation informational representations, (i) utilizing informational representations that were derived from the processing of data from first-series observations or second-series observations, (j) utilizing standard informational representations or definitions regarding or utilizing a complete spectrum of aspects of the operations of universal health metrics monitors, or (k) utilizing standard units of measure or methods of making measurements in the making of measurements regarding or utilizing sensor observations or sensor observation subjects.

Universal health metrics monitors are configurable for utilizing non-universal health metrics monitor standard tools, methodologies, or programming. However, informational representations regarding or utilizing sensor observations or sensor observation subjects from non-universal health metrics monitor standard tools, methodologies, or programming will need to be either an exact match to or translated or adjusted to match the standard informational representations that are assigned or utilized by universal health metrics monitors.

Universal health metrics monitors are configurable for being reasonably persistent in attempting to achieve selected health determination goals. As an example, should a selected health determination based upon conclusions from comparing informational representations regarding measure points or analytically rich aspects, characteristics, or features from first-series observations of one specific person not result in the making of a selected health determination, then universal health metrics monitors are configurable for continuing comparing or determining operations until the selected health determination has been made or there are no further comparable first-series observation datasets to compare to available second-series observation datasets.

The spectrum of sensors or sensor observation data that universal health metrics monitors are configurable for utilizing includes (a) light sensors that sense any spectra of light, (b) odor sensors, (c) temperature sensors, (d) pressure sensors, (e) energy sensors, (f) image sensors that utilize any spectra of light, (g) chemical sensors, or (h) a complete spectrum of other types of sensor that can be used in the capturing of sensor observations that are utilizable by universal health metrics monitors in their making of selected health determinations.

Universal health metrics monitors are configurable for interacting with cyber resources that are being utilized by the universal health metrics monitors. The interacting can be utilized for altering the operations of those cyber resources for any purpose, including to capture any possible sensor observations or providing any useful variations of operations of universal health metrics monitor resources.

Through the incredible speed and power of cyber resources, any large number of criteria can be collectively or selectively utilized for any aspects of the operations of universal health metrics monitors.

All aspects of operations of universal health metrics monitors can be configurable for utilizing selected choices of predetermined criteria. Criteria are selected from a complete spectrum of criteria (a) by people, (b) as an integral part of the operations of cyber resources that are utilizing or being utilized by universal health metrics monitors, (c) as part of the operations of universal health metrics monitors, (d) by utilizing any other means for selecting criteria, or (e) combinations thereof. Selection of any aspect of operations of universal health metrics monitors constitutes selecting criteria.

Criteria are selected choices of who, when, where, what, why, or how as each relates to any aspect of operations of universal health metrics monitors. Providing a choice of any possible criteria and any criteria being possible can well be the most important feature that the entire family of cyber resources has to offer. Universal health metrics monitors are configurable for taking full and best advantage of this particular cyber feature by providing users with choices of selections of available criteria regarding any aspects of utilization of universal health metrics monitors.

Universal health metrics monitors are configurable for utilizing useful information from any source in their making of selected health determinations regarding or utilizing sensor observations or people who are subjects of sensor observations.

Universal health metrics monitors are configurable for storing data or datasets utilizing tools, methodologies, or programming from a complete spectrum of tools, methodologies, or programming that are utilized for storing data or datasets.

Universal health metrics monitors are configurable for storing informational representations as data, utilizing storage media from a complete spectrum of types or variations of utilizable storage media.

Universal health metrics monitors are configurable for storing data or datasets for any duration of time.

Universal health metrics monitors are configurable for standardizing any or all aspects of any or all storage operations or storage resources. Standardization of all aspects of all storage operations or storage resources enables storage operations to be performed at the highest attainable percentages of accuracy, reliability, efficiency, interoperability, or simplicity.

Universal health metrics monitors are configurable for utilizing data regarding previous same measurements in their making of selected health determinations regarding or utilizing changes in same measurements that occur over time. Therein lies one of the more powerful features of the analyzing operations of universal health metrics monitors—selected health determinations that are made utilizing changes in measurements or changes in patterns of measurements that occur over time. Measured changes are utilizable by universal health metrics monitors in their making of selected health determinations.

Analysis of changes that occur over time is an indispensable part of the accurate or reliable making of a multitude of selected health determinations. Many of these determinations cannot be made by prior art because much of prior art is not configured or configurable for making selected health determinations that utilize changes to same sensor observations or same sensor observation subjects that occur over time.

Universal health metrics monitors are configurable for performing analysis of sensor observation-derived representations to identify tells that are accurately or reliably utilizable in their making of selected health determinations.

Sensor-observable tells that are located through utilization of measure points on sensor observation-derived representations include (a) distances or changes in distances between measure points, (b) angles or changes in angles where two or more lines between measure points either cross or meet each other, (c) levels or changes in levels of red, green, or blue light at one or more pixels at the locations of or in areas that are located through utilization of measure points, (d) pressures or changes in pressures at or in the areas of measure points, (e) temperatures or changes in temperatures at or in the areas of measure points, or (f) any other measurable changes to analytically rich aspects, characteristics, or features that are utilizable as tells, wherein the same measurable sensor-observable tells consistently or reliably are present with same or similar events, actions, circumstances, or combinations thereof.

Selections of the determinations that are to be made through utilization of sensor observations are made by (a) tools, (b) methodologies, (c) programming, (d) people, or (e) combinations thereof.

Determinations regarding which analytically rich aspects, characteristics, or features of or from sensor observation-derived representations will be located through utilization of measure points are made by at least one member selected from the group consisting of (a) tools, (b) methodologies, (c) programming, (d) people, or (e) combinations thereof.

Informational representations regarding or utilizing selected measure points are utilizable by universal health metrics monitors in their making of selected determinations regarding or utilizing at least one member selected from the group consisting of (a) the locations of selected measure points, (b) a measure point's measured relationship with other measure points, (c) the exact point where a measure point locates analytically rich aspects, characteristics, or features of or from sensor observation-derived representations, (d) areas of analytically rich aspects, characteristics, or features of or from sensor observation-derived representations that are located through utilization of measure points, (e) analytically rich aspects, characteristics, or features of or from sensor observation-derived representations that are separated by lines between two or more measure points, (f) sensor observation-derived representations of odors, (g) sensor observation-derived representations of pressures, (h) sensor observation-derived representations of temperatures, or (i) any other sensor observation-derived representations of analytically rich aspects, characteristics, or features of or from sensor observation-derived representations that are located through utilization of measure points.

Universal health metrics monitors are configurable for utilizing the smallest possible number of informational representations regarding the smallest possible number of selected analytically rich aspects, characteristics, or features of or from the smallest possible number of sensor observation-derived representations as are needed for their making of the smallest possible number of intermediate cyber determinations that are needed for their making of selected final cyber determinations regarding or utilizing sensor observations or the health of people who are subjects of sensor observations.

Further, universal health metrics monitors are preferably configured for providing or utilizing concise datasets, wherein the informational representations from concise datasets are as analytically rich as needed for utilization in the making of selected health determinations and concise to the point where, if there were any fewer informational representations, it would not be possible to make selected health determinations accurately or reliably. Additionally, concise datasets are preferably configurable to include few if any unnecessary informational representations.

Universal health metrics monitors are configurable for utilizing informational representations from original sensor observation datasets that range from being the least complex, regarding overall size or complexity, to being extremely complex, regarding its overall size or complexity. A temperature sensor observation is an example of a very small and simple set of informational representations from sensor observations, wherein universal health metrics monitors are configurable for assigning appropriate informational representations regarding the specific times temperature sensor observations indicated temperatures increased or decreased one-tenth of a degree.

Video-formatted image sensor observations are an example of very large and complex original sensor observation datasets. As an example, a 1080p video-formatted image sensor is configured for providing a stream of 30 sequential two million-pixel images per second. These images have standard information regarding each pixel which includes the pixel's horizontal and vertical line locations, as well as its observed levels of red, green, and blue light.

Universal health metrics monitors are configurable for compressing very large original sensor observation datasets into concise datasets. This practice yields many advantages which include (a) concise working datasets; as an example, 1080p video sensor observations of a person's face can be compressed down to concise working datasets regarding a standard target set of 17 facial measure points; wherein universal health metrics monitors compress the original sensor observation datasets that are comprised of informational representations regarding more than two-million pixels per image down to concise working datasets that are comprised of sensor data regarding only 17 selected pixels from each image, (b) reduction of the amount of data that is stored or used in the making of selected health determinations, (c) reduction in the amount of data that is processed in the making of selected health determinations; it is much more efficient to store, process, or use informational representations regarding the 17 pixels at the 17 selected facial measure points than it is to store, process, or use informational representations regarding each of the more than two million pixels that make up the original sensor observation dataset for each video image, (d) many health determinations cannot be made by prior art, but they can be made by universal health metrics monitors through their utilization of concise datasets or measure points, or (e) any other advantages that the compressing of very large sensor observation datasets into analytically rich concise datasets enables.

Universal health metrics monitors may utilize concise datasets that are comprised of selected sensor data or derived data.

Selected sensor data are comprised of informational representations that have been selected from original sensor observation datasets by tools, methodologies, programming, or people.

Selected sensor data are preferably configurable for being comprised of the smallest possible amount of data that will be needed for the accurate or reliable making of selected determinations regarding or utilizing sensor observations or the health of people who are subjects of sensor observations. When using selected sensor data regarding only 17 pixels from each sequential video image of a person's face, one might think that this small amount of sensor data would be useless in the making of almost any selected health determination. However, with analysis over time, the selected sensor data regarding the 17 pixels is analytically rich, and through utilization of extreme analysis tools, methodologies, or programming, universal health metrics monitors are configurable for deriving a multitude of analytically rich data from the 17 facial pixels—data that are indispensable to universal health metrics monitors in their making of a multitude of selected health determinations.

Extreme analysis is the processing of selected sensor data or derived data, wherein the processing results in the creation of derived data that are then included in concise datasets. Further, most if not all derived data may be derived utilizing the extreme analysis tools, methodologies, or programming resources of universal health metrics monitors.

Using one measure point that locates a representation of a pulse point on a sensor observation-derived representation of a person's face as an example, the following determinations can be made (a) increases in the observed level of red light at the pixel where the pulse point is located can be used for determining every time a pulse occurs, (b) the number of pulses that occur per minute, (c) the average pulse rate for an hour, day, week, during a workout, or when sleeping, (d) determinations regarding blood pressure can be made using a 23-pixel column or row of pixels with the measure point at its center, (e) the average blood pressure for an hour, day, week, during a workout, or when sleeping, (f) patterns of changes in pulse rate or blood pressure, (g) changes in patterns of pulse rate or blood pressure over periods of time, including over weeks, months, or years.

These or other extreme analysis-derived informational representations can be included as derived data in concise datasets where they can be used by universal health metrics monitors in real time or at times thereafter in the making of selected health determinations.

Measure points are usable for purposes from a complete spectrum of purposes for which measure points that are used in the locating of selected analytically rich aspects, characteristics, or features of or from sensor observation-derived representations can be used.

Determinations regarding which measure points or target sets of measure points will be used are made by at least one member selected from the group consisting of (a) people, (b) tools, (c) methodologies, (d) programming, or (e) combinations thereof.

Measure points provide the structure, continuity, or common elements that are needed to standardize or unify the different operations of universal health metrics monitors when those operations are performed at different times or under the same or different observation circumstances. Through use of the standardization or the structure that is enabled by utilization of measure points, universal health metrics monitors are configurable for utilizing the same standard tools, methodologies, or programming in the making of same or similar selected health determinations.

The structure that is provided by utilization of measure points or target sets of measure points enables interoperable use of the disclosed universal health metrics monitors tools, methodologies, or programming across a complete spectrum of systems or environments. Utilization of measure points provides the structure and common elements that are needed to (a) standardize, (b) unify, or (c) synchronize the operations of the different tools, methodologies, or programming of the disclosed universal health metrics monitors whenever or wherever they are performed.

A spectrum of purposes for which measure points can be used by universal health metrics monitors in their making of selected health determinations includes (a) providing points from which to measure, including measurements of light, temperatures, pressures, colors, odors, chemical signatures, distances, degrees of angles, locations, orientations, times, or any other measurements from a complete spectrum of measurements where measure points can be utilized, (b) locating, on image sensor-derived representations, the corners or boundaries of selected areas of pixels or scalable configurable grids, (c) locating, from image sensor-derived representations, differences or patterns of differences between adjoining pixels that indicate edges or other selected analytically rich aspects, characteristics, or features, (d) being parts of standard target sets of measure points, (e) identifying measure points from standard target sets of measure points whose corresponding analytically rich aspects, characteristics, or features could not be located on sensor observation-derived representations, or (f) being used for purposes from a complete spectrum of other purposes for which measure points that are used in the locating of analytically rich aspects, characteristics, or features of or from sensor observation-derived representations can be used.

Measure points can be utilized by universal health metrics monitors in their making of selected measurements, whereby informational representations regarding results of measurements are stored or utilized by universal health metrics monitors in their making of selected health determinations. Examples of measurements regarding or utilizing observed analytically rich aspects, characteristics, or features of or from sensor observation-derived representations that are usable by universal health metrics monitors in their making of selected health determinations include (a) measured odors, (b) measured chemical signatures, (c) measured temperatures, (d) measured pressures, (e) measured colors, (f) measured levels of colored light, (g) measured brightness, (h) measured distances between measure points, (i) measured angles where lines between measure points cross or meet, (j) measured speeds, (k) measured time, or (l) any other measurements regarding or utilizing measure points. In addition, universal health metrics monitors are configurable for utilizing changes to selected measurements that occur over time in their making of selected health determinations.

Universal health metrics monitors are configurable for determining where to locate measure points on sensor observation-derived representations where they can best be utilized in the locating of sensor-observable changes or tells that reliably occur over any part of a series of sensor observation-derived representations. Universal health metrics monitors are configurable for utilizing selected tells in their making of selected health determinations.

Universal health metrics monitors are configurable for utilizing measure points at only the analytically rich aspects, characteristics, or features that are needed for their making of selected health determinations.

Determinations regarding which analytically rich aspects, characteristics, or features of or from sensor observation-derived representations will be located through utilization of measure points are made by at least one member selected from the group consisting of (a) people, (b) tools, (c) methodologies, (d) programming, or (e) combinations thereof.

Guiding factors for determining which analytically rich aspects, characteristics, or features of or from sensor observation-derived representations will be located through utilization of measure points includes (a) which analytically rich aspects, characteristics, or features of or from sensor observation-derived representations are needed in the making of selected health determinations, (b) which sensor-observable changes that occur over time are utilizable in the making of selected health determinations, (c) which analytically rich aspects, characteristics, or features that are locatable through utilization of measure points are present or observable in similar sensor observations or sensor observation subjects, (d) whether all or most similar sensor observations or people who are subjects of sensor observations have the same or similar analytically rich aspects, characteristics, or features to locate through utilization of measure points, (e) whether the standard tools, methodologies, or programming of universal health metrics monitors are utilizable for the selecting of the analytically rich aspects, characteristics, or features to utilize, or (f) whether any other factors exist that influence the selection of which analytically rich aspects, characteristics, or features of or from sensor observation-derived representations will be located through utilization of measure points.

When utilizing video-formatted image sensor observations of a person's face to determine whether said person is falling asleep, the universal health metrics monitor need only utilize two analytically rich features in their making of the selected determinations. The first analytically rich feature is the bottom center of one of the person's upper eyelids; the second analytically rich feature is the top center of the lower eyelid of the same eye. Universal health metrics monitors utilize measure points in their locating of both analytically rich features. The distance between these two measure points is utilized by universal health metrics monitors in their making of selected determinations as to whether the person's eyelids are closed. Should the person's eyelids be determined to be closed for a specified duration of time or longer, then universal health metrics monitors are configurable for determining that the person is falling asleep or has fallen asleep.

It may be quite simple for a person to determine where measure points should be located on sensor observation-derived representations. As in the previous example, a person's selection of the two specific measure points enabled the universal health metrics monitors to utilize a simple, concise, and efficient combination of sensor-observed behaviors that were compressed into a few standard informational representations that are utilizable by universal health metrics monitors in their making of the selected cyber determinations as to whether or not a person is falling asleep or has fallen asleep.

Universal health metrics monitors are configurable for selecting and utilizing standard target sets of measure points. Selecting and utilizing standard target sets of measure points is done for the purposes of (a) including in standard target sets only the measure points that might be possible to locate on specific sensor observation-derived representations that are observed under specific observation circumstances; for example, a different standard set of measure points is utilized for a full-frontal representation of a person's face than would be utilized for a side view of the same person's face and head, (b) including in standard target sets only the measure points that are needed in the making of selected health determinations; for example, standard target sets of measure points that are used in locating the centers of pupils and the inside or outside corners of eyes are utilizable in the making of selected determinations regarding the direction, in terms of up, down, left, or right, that a person is looking, (c) determining exactly what a person is looking at, (d) locating specific occurrences such as selected increments of time that have elapsed or selected increments of change in temperature that have occurred since the most recent measure point was located on a temperature sensor observation representation, (e) determining which standard target sets of measure points to utilize in the processing of second-series observations that will be compared to specific first-series observations; wherein in an effort to achieve a highest attainable percentage of cyber determination accuracy, universal health metrics monitors are configurable for utilizing the same standard target set of measure points that were used for first-series observations for the analysis of comparable second-series observations, or (f) for purposes from a complete spectrum of other purposes for which selecting or utilizing standard target sets of measure points can be used in the operations of universal health metrics monitors.

The points on sensor observation-derived representations upon which selected measure points are located can differ substantially under different observation circumstances. It is therefore necessary for universal health metrics monitors to be configurable for utilizing more than one standard target set of measure points for the same observation, but under differing observation circumstances, with each different standard target set of measure points being configured to enable the accurate or reliable making of selected health determinations regarding or utilizing the same or similar sensor observations or sensor observation subjects, but under different observation circumstances.

Determinations regarding which measure points will be included in each standard target set of measure points are made by at least one member selected from the group consisting of (a) people, (b) tools, (c) methodologies, (d) programming, or (e) combinations thereof.

Universal health metrics monitors are configurable for locating every measure point from a standard target set that can be located. Informational representations regarding measure points from standard target sets that universal health metrics monitors were unable to locate can also be stored or utilized in the making of selected health determinations.

Universal health metrics monitors are preferably configurable for utilizing as few target sets of measure points as can possibly be used in their accurate or reliable making of selected health determinations; wherein each standard target set of measure points preferably includes as few measure points as could possibly be used by universal health metrics monitors in their accurate or reliable making of selected health determinations.

Standard target sets of measure points add the structure that universal health metrics monitors need to process comparable first-series sensor observations and second-series sensor observations in the same way.

Universal health metrics monitors are configurable for assigning or utilizing standard measurements, standard designations, standard informational representations, or standard definitions to represent observations, subjects of observations, measure points, measurements, or any other analytically rich aspects, characteristics, or features of or from universal health metrics monitors' operations.

The appropriate standard informational representations to assign to analytically rich aspects, characteristics, or features are selected by at least one member from the group consisting of (a) people, (b) tools, (c) methodologies, (d) programming, or (e) combinations thereof.

Standard informational representations that are assigned or utilized include (a) informational representations identifying the specific sensor observation with which informational representations are associated, (b) informational representations identifying the specific time or times that specific sensor observations or parts thereof were captured, (c) informational representations regarding the sensors that were utilized in the making of observations, (d) informational representations regarding the circumstances of sensor observations, (e) informational representations regarding which standard target sets of measure points were utilized, (f) informational representations regarding the tools, methodologies, or programming that were utilized, (g) informational representations regarding selected analytically rich aspects, characteristics, or features, (h) informational representations regarding analytically rich aspects, characteristics, or features at the locations of measure points or in areas that are located through utilization of measure points, (i) informational representations regarding measured locations or measured orientations of measure points that are at the exact locations of, or in the areas of selected analytically rich aspects, characteristics, or features of or from sensor observation-derived representations, (j) informational representations regarding measured locations or measured orientations of measure points on sensor observation-derived representations, or in relation to other analytically rich aspects, characteristics, or features that are located by measure points on the same or different sensor observation-derived representations, or (k) informational representations from a complete spectrum of informational representations regarding or utilizing other analytically rich aspects, characteristics, or features of or from measure points, sensor observations, sensor observation subjects, or sensor observation-derived representations.

Utilization of only one standard set of informational representations is an important part of accurately, reliably, and consistently making selected health determinations. Universal health metrics monitors are configurable for making on a worldwide basis consistent and accurate assignments of standard informational representations to any analytically rich aspect, characteristic, or feature of or from sensor observation-derived representations of people.

Universal health metrics monitors are configurable for utilizing standard adjusting factors to compensate for differences between second-series observation circumstances and first-series observation circumstances. This includes differences in (a) lighting, (b) pose, (c) location, (d) movement of sensors, (e) movement of subjects of sensor observations, (f) parts of observation subjects that were observed, (g) wind conditions, (h) sensors that were used for observations, or (i) other differences between second-series observation circumstances and first-series observation circumstances that can be compensated for through utilization of standard adjusting factors.

Typically, universal health metrics monitors break down their processing of sensor observation data into three areas of operations (a) the making of selected initial determinations, (b) the making of selected intermediate determinations, and (c) the making of selected final health determinations. In some cases, all or any part of what was determined when making initial determinations will result in the making of at least one selected intermediate determination. Further, the making of any one or more intermediate determinations can also result in the making of one or more selected final health determinations.

Universal health metrics monitors are configurable for reporting on or otherwise utilizing results from: initial determinations, intermediate determinations, and final health determinations.

Universal health metrics monitors are configurable for providing the highest attainable percentages of simplicity, efficiency, accuracy, or reliability in their making of selected determinations regarding or utilizing sensor observations or the health of people who are subjects of sensor observation. They do so, in part, by only performing analysis of the specific sensor observation data that are needed in their making of selected health determinations. Therefore, universal health metrics monitors do not perform analysis of sensor data that is not utilized in their making of selected health determinations.

Universal health metrics monitors are configurable for making selected determinations that are not possible to make utilizing measure points from image sensor observation-derived representations. When it is not possible to make selected health determinations utilizing measure points, then universal health metrics monitors are configurable for analyzing selected groups of pixels utilizing tools, methodologies, or programming from a complete spectrum of other tools, methodologies, or programming that can be utilized by universal health metrics monitors in their selecting of, locating of, or using of pixels, groups of pixels, or other sensor observation data.

Universal health metrics monitors are configurable for utilizing three general categories of tools, methodologies, or programming for accurately or reliably locating measure points on sensor observation-derived representations of people who are subjects of sensor observations:
  (a) personalized tools, methodologies, or programming that are configurable for accurately or reliably and exclusively locating selected measure points on sensor observation-derived representations of only one specific person,
  (b) group tools, methodologies, or programming that are configurable for accurately or reliably locating selected measure points on sensor observation-derived representations of any person from specific groups of people, or
  (c) generalized tools, methodologies, or programming that are configurable for accurately or reliably locating selected measure points on sensor observation-derived representations of any people.

Universal health metrics monitors are configurable for achieving highest attainable percentages of accuracy goals when making selected health determinations through their use of standard tools, methodologies, or programming that have been trained, taught, or configured for accurately or reliably locating selected measure points on sensor observation-derived representations of only one specific person.

Universal health metrics monitors are configurable for providing or utilizing standard tools, methodologies, or programming that are trained, taught, or configured for exclusively locating selected measure points on sensor observation-derived representations of only one specific person. Utilization of personally trained, taught, or configured tools, methodologies, or programming is a necessary part of making selected health determinations regarding or utilizing the one specific person at the highest attainable percentages of accuracy or reliability.

Universal health metrics monitors are configurable for locating measure points on sensor observation-derived representations of people, or the sensor observation itself, at the highest attainable percentages of accuracy.

The personalized tools, methodologies, or programming of universal health metrics monitors are configurable for brief utilization, wherein the tools, methodologies, or programming learn, are taught or are configured for the accurate or reliable locating of selected measure points for a brief period such as, for example, facial identity testing for one-time access to a building.

Two types of basic operations can be used when locating measure points on video-formatted image sensor observations: the first operation utilizes tools, methodologies, or programming to determine the exact initial locations to place selected measure points on one or more sensor observation-derived representations; the second utilizes tracking tools, methodologies, or programming to predict or determining the points where selected measure points are to be located on subsequent sequential sensor observation-derived representations. Should tracking operations be interrupted, then the exact locations of measure points can be determined by performing the processes or procedures that initially determined the locations to place selected measure points.

Universal health metrics monitors are further configurable for constantly or intermittently utilizing initial locating processes or procedures for determining the exact points on each sensor observation-derived representation upon which selected measure points are to be located.

Examples of where universal health metrics monitors may locate measure points on temperature sensor observation-derived representations include (a) the temperature when a sensor observation begins, (b) the time when a sensor observation begins, (c) any point in time when there is a one-tenth degree change from the most recent measure point identified temperature, (d) the temperature when a sensor observation ends, (e) the time when a temperature sensor observation ends, or (f) any other points from temperature sensor observation-derived representations where universal health metrics monitors can utilize measure points in their making of selected health determinations.

When universal health metrics monitors are utilized for making selected determinations regarding or utilizing temperature sensor observations, the locating of measure points on sensor observation-derived representation is straightforward; therefore, complex tools, methodologies, or programming are not needed for reliably or consistently locating measure points at 100% accuracy. However, the making of selected health determinations that utilize video-formatted image sensor observations of a person's face require utilization of complex combinations of standard tools, methodologies, or programming for accurately or reliably locating or utilizing selected measure points at the highest percentages of accuracy.

Universal health metrics monitors are configurable for utilizing summation table analysis in conjunction with scalable configurable grids in their making of selected predictive determinations regarding where to locate selected measure points on subsequent sequential sensor observation-derived representations. Further, universal health metrics monitors are configurable for utilizing smudge analysis, darkest pixel analysis, lightest pixel analysis, or any methods of analysis, from a complete spectrum of other methods of analysis that can be utilized for predicting or determining where to locate selected measure points on subsequent sequential sensor observation-derived representations.

Utilization of measure points for accurately or reliably locating selected analytically rich aspects, characteristics, or features of or from sensor observation-derived representations is not the only combination of tools, methodologies, or programming that universal health metrics monitors are configurable for utilizing in their making of selected health determinations. Universal health metrics monitors are configurable for making selected health determinations through utilization of tools, methodologies, or programming from a complete spectrum of tools, methodologies, or programming that can be utilized in their making of selected health determinations.

At the heart of most cybersecurity failures is a complete inability of computers or cyber resources to authenticate the claimed identity of any one specific person constantly and accurately prior to allowing that person or the cyber devices of that person to gain initial access and/or continued access. Universal health metrics monitors can be configured for accurately and constantly authenticating one specific person's identity as a prerequisite to that person having initial and then continued access to any resources of universal health metrics monitors.

The key to accurately or reliably authenticating any one specific person's identity is through the utilization of sensor observations of the unique physical, visual, behavioral, physiological or biological aspects, characteristics, or features of the person whose identity is being authenticated.

Universal health metrics monitors are configurable for making selected determinations regarding the identity of one specific person (identity tests). These identity tests are utilizable for accurately granting only selected specific known people access to specific universal health metrics monitors, thereby preventing all others from gaining similar access.

The key to enabling a high degree of privacy and security when utilizing universal health metrics monitors is to require that selected people constantly pass their own identity tests prior to being granted initial or continued access to selected resources of universal health metrics monitors.

Universal health metrics monitors are configurable for making 100% accurate determinations regarding the identity of any one specific person and they are configurable for doing so utilizing as few or as many unique physical, visual, behavioral, physiological, or biological characteristics of a person as are necessary to achieve attainable identity test goals. When internal and external sensor observations (which can include visual, biological, or physiological sensor observations) of a person are utilized, a very large number of possible unique combinations of analytically rich aspects, characteristics, or features of any one specific person can be utilized by universal health metrics monitors in their making of determinations of identity. Every unique sensor-observed physical, visual, behavioral, physiological, or biological characteristic of a person is a means for accurately making selected determinations of identity regarding the one specific person.

Using video-formatted image sensor observation of a person's face as an example, universal health metrics monitors accurately or reliably locate a preferred standard target set of 17 measure points on each sequential sensor observation-derived frontal representation of a person's face from a video stream. One selection of locations for 17 facial measure points includes corners of eyes, centers of pupils, bottom centers of upper eyelids, top centers of lower eyelids, tip of nose, centers of left and right jawlines, corners of mouth, top center of upper lip, and bottom center of lower lip.

Utilizing universal health metrics monitors' concise datasets regarding the X and the Y line locations of the 17 measure points and the observed levels of red, green, or blue light at each of the 17 pixels where the selected measure points are located, enables universal health metrics monitors to constantly make determinations of identity as well as a multitude of other selected health determinations regarding the person who is the subject of the identity test—many of which have not and cannot be made by prior art.

Informational representations regarding any one specific first or second-series observation subject can be used as the cyberspace identifiers or the cyberspace identity of the one specific observation subject. These cyberspace identifiers can be used to replace the identifiers that are now used such as social security numbers, birth dates, or driver's license numbers, all of which can be easily stolen or replicated and maliciously used by others.

Far more selected health determinations can be made about a specific person through utilization of universal health metrics monitors' concise datasets regarding the 17 facial pixels than can be made by prior art through prior art's utilization of the entire two million pixel-per-image datasets upon which the 17 facial pixels were located.

Universal health metrics monitors are configurable for making selected health determinations utilizing available sensor observations. Operations of universal health metrics monitors can begin with selection of which health determinations are to be made. Examples of selected health determinations that could be made utilizing image sensor observations of a person's face include what is (a) a person's identity, (b) a person's hair color, (c) a person's eye color, (d) a person's facial expression, (e) a person's mental or physical state of health, (f) a person's pulse rate, or (g) a person's blood pressure.

Examples of analytically rich aspects, characteristics, or features from sensor observation-derived representations of people's faces that can be located through utilization of measure points include (a) corners of eyes, (b) centers of pupils, (c) tips of noses, (d) corners of mouths, (e) top centers of upper lips, (f) bottom centers of lower lips, (g) tips of chins, (h) edges of jawlines, (i) top centers of eyebrows, (j) outer edges of eyebrows, (k) inner edges of eyebrows, (l) pulse points, (m) scars, (n) marks, or (o) tattoos.

There are a multitude of determinations that can be made regarding people including (a) identity, (b) hair color, (c) moles, (d) wrinkles in skin, (e) freckles, (f) axis points or geometries at joints, (g) scars, (h) height, (i) eye color, (j) pulse rate, (k) blood pressure, (l) blood sugar level, or (m) sensor-observable aspects, characteristics or features of people and people's health from a complete spectrum of other sensor-observable aspects, characteristics, or features of people and people's health.

Measurements from sensor observation-derived representations can be utilized by universal health metrics monitors in their making of a multitude of selected determinations. One example is the utilization of facial observations to determine exactly where a person is looking. To do so only requires the use of four measure points that locate four selected analytically rich features from sensor observation-derived representations of a person's face; wherein one measure point is selected to be located at a representation of the center of one pupil and one measure point is selected to be located at a representation of the inner corner of the same eye. These two measure points are utilized by universal health metrics monitors to determine if the person is looking to the left, straight ahead, or to the right, and to determine if the person is looking up, straight outward, or looking down. The third measure point is selected to be located on a representation of the tip of the person's nose, and the fourth measure point is selected to be located at a representation of the center of their left or right jawline. Distances between the third and fourth measure points are utilized to determine if the person's head is turned to the left, not turned at all, or turned to the right. Further, the difference between the horizontal line location where the measure point at the tip of the nose is located, and the horizontal line location where the measure point at the center of the jawline is located are utilized by universal health metrics monitors for determining if the head is tilted up, not tilted, or is tilted down. Universal health metrics monitors are configurable for utilizing data regarding only the four pixels where the four selected measure points are located for determining precisely where a person is looking.

Universal health metrics monitors can utilize changes that occur over long periods of time; for example, measurements of the range of a person's facial movements over several years can be used to determine that a person has an early onset of Parkinson's Disease. Universal health metrics monitors can make that determination at the earliest point in time that Parkinson's Disease is sensor-detectable. A multitude of health determinations that utilize people who are subjects of sensor observations can only be made through utilization of analysis of changes that occur over time. Universal health metrics monitors are configurable for quickly, efficiently, or reliably utilizing measure points or concise datasets in their accurate or reliable making of health determinations from a complete spectrum of health determinations that can be made regarding people who are subjects of sensor observations.

Should it be found that specific image sensor-observable rapid eye movement patterns are accurate or reliable indicators that a person has a particular mental distress, then image sensors that capture video-formatted images of a person's eyes at a rate of 500 sequential images each second could be utilized by universal health metrics monitors in their locating of a standard target set of only two measure points. One measure point locates the center of a sensor observation-derived representation of a pupil, and a second measure point locates a sensor observation-derived representation of the inside or outside corner of the same eye. Universal health metrics monitors are configurable for utilizing the horizontal and the vertical line locations on a pixel grid of those two measure points in their accurate or reliable making of selected determinations regarding whether or not a person has rapid eye movement patterns that reliably indicate their particular mental distress.

Further, the rapid eye movement patterns that might indicate a specific person's particular mental distress could also be detected using video that is captured at the rate of only 30 or 60 sequential images per second. Universal health metrics monitors are configurable for utilizing smudge analysis in conjunction with scalable configurable grids; wherein one measure point locates a specific point on sensor observation-derived representations where the white of an eye and the iris meet. Universal health metrics monitors are configurable for performing analysis of patterns of, variations in, or smudges in, observed levels of red, green, or blue light from the area of the sensor observation-derived representations where the measure point is located. As an example, sensor observation data from each pixel within a 15-pixel square that includes the selected measure point at its center could be utilized by universal health metrics monitors in their making of selected real-time health determinations as to whether a sensor-observed person is mentally distressed.

Universal health metrics monitors are further configurable for utilizing standard target sets of measure points that comprise only one measure point. This single measure point is utilized for enabling operations of a human fingertip-controlled touchless user interface. A person who is using a universal health metrics monitor that is running the touchless user interface application is used as an example. Their universal health metrics monitor's camera captures video at a rate of 30 images per second. The universal health metrics monitor's touchless user interface application is configured for recording to concise datasets the horizontal and the vertical pixel grid line locations of the one pixel at the center of the tip of the person's index finger. These operations are performed for each sequential image at a rate of 30 or more images per second. When the person moves their finger, the updated fingertip location is then utilized to similarly relocate a cursor on the universal health metrics monitor's image display.

Concise datasets for touchless user interfaces are derived from each sequential image of a sensor's observations and they may only include data regarding the X and the Y line locations along with the measured levels of red, green, or blue light at the one pixel.

Universal health metrics monitors are configurable for enabling a person to utilize a video camera capturing movement of the person's fingertips to move a cursor or make a selection at the location of the cursor, and they do so without the need for finger-to-touchscreen contact. To make a selection at a current cursor location, all a person needs to do is to move their finger closer to and then farther away from the camera.

Changes in measured levels of red, green, or blue light at the pixel where the single measure point locates the center of a fingertip are used by universal health metrics monitors for determining that a person wishes to make a selection at the cursor's location.

Examples of prior art human-to-machine user interface devices whose full range of functions can be replicated by a universal health metrics monitor's utilization of one or two fingertips include (a) mouse interface devices, (b) trackball interface devices, (c) touch screen interface devices, (d) stylus interface devices, (e) keyboard interface devices, or (f) other human-to-machine interface devices whose functions can be replicated through utilization of universal health metrics monitors and a person's intentional movement of their fingertips.

Use of touchless user interface technology is not limited to one fingertip, nor is it limited to fingertips. Touchless user interface applications of universal health metrics monitors can also be configured for utilizing any or all fingertips, the tips of noses, elbows, gaze of eyes, or any other sensor-observable, analytically rich aspects, characteristics, or features of people that can be used to communicate people's intentions to interact with universal health metrics monitors. Touchless user interfaces can also be configured to offset some or all disabled people's disabilities when interacting with universal health metrics monitors or any other cyber device or resource that utilizes user interfaces.

Working datasets for single fingertip-controlled touchless user interface applications of universal health metrics monitors are configurable for having the highest amount of compression of data from video images that will ever exist: compression at a ratio of N to one, where N is the total number of pixels from each original video-formatted image, and one is the number of pixels from the working datasets regarding the one single pixel that a measure point locates at the center of a fingertip; wherein, when using 1080p video, the compression ratio of a universal health metrics monitors touchless user interface's working dataset is over two million-to-one.

The foregoing principles are further appreciated with respect to FIG. 1, which illustrates a first particular, non-limiting embodiment of utilization of one configuration of a touchless user interface in accordance with the teachings herein. As seen therein, a desktop-configured health metrics monitor 103, equipped with an image display screen 105, and a video-formatted image sensor 107. The health metrics monitor 103, has installed, in a tangible, non-transient memory device associated therewith, universal health metrics monitor programming that implements the tools, methodologies, or programming of a human fingertip-to-universal health metrics monitor touchless user interface application. Accordingly, the health metrics monitor 103, utilizes the original sensor observation datasets from its image sensor's observations of a person's fingertip in its locating of a measure point, at the one pixel from the image sensor observation-derived representations, that is at the center of each sequential sensor observation-derived representation of the person's fingertip 109. The touchless user interface utilizes the X and the Y line locations of the pixel as a reference for similarly locating a cursor on the pixel grid of the image display screen 105. The location of the cursor is updated from video image to sequential video image, when there has been a change in the location of the measure point on the sensor observation-derived representation's pixel grid. The person makes a selection at the location of the cursor by quickly moving their fingertip closer to and then farther away from the image sensor. Changes in measurements of observed levels of red, green, or blue light at the pixel where the measure point is located enable the touchless user interface to determine that the person wishes to make a selection where the cursor is located on the image display screen. In this depiction the user's finger is utilized as an alternative to a mouse or stylus for drawing, although it will be appreciated that the same or similar techniques can be utilized for a wide variety of other purposes.

The concise, efficient, and simple tools and methodologies of touchless user interfaces are also utilizable for accurately authenticating the identity of any one specific person. One example of how universal health metrics monitors may perform identity authentications requires a person to sign their name in the air for observation by a video camera. Many factors are utilized for comparing a specific yet-to-be-identified person's signature to the signature of any one specific known person that the yet-to-be-identified person claims to be. Analytically rich aspects, characteristics, or features that are utilized by universal health metrics monitors in their making of the selected cyber identity authentication determinations include (a) the line pattern of the signature, (b) behavioral characteristics of movement, including movement toward and away from the camera, (c) cadence, (d) speed, or (e) timing. Utilizing comparison of second-series observation signatures to first-series observation signatures enables the making of selected identity determinations at the highest attainable percentages of accuracy or reliability. Utilization of the movement of only one fingertip-located measure point is only one method that universal health metrics monitors can be configured to use for providing 100% accurate identity authentication. This simple methodology can be used to eliminate fraud, unwanted access, and establish accountability. Universal health metrics monitors can be configured to perform identity authentications utilizing a number of methodologies that are as simple, concise, and efficient as possible.

Universal health metrics monitors are configurable for making selected sensor data-derived health determinations that have not been made or cannot be made by prior art. Further, universal health metrics monitors' processes or procedures are configurable for being as simple, concise, efficient, and accurate as possible.

The tools, methodologies, and programming that are utilized by universal health metrics monitors operate differently than the tools, methodologies, and programming of prior art, yet universal health metrics monitors are utilizable for making the same selected cyber determinations as can be made by prior art. Universal health metrics monitors do so, in part, by using tools, methodologies, and programming that utilize measure points in the locating of selected analytically rich aspects, characteristics, or features of or from sensor observation-derived representations. Universal health metrics monitors also utilize datasets that are configured or structured for consistently being utilizable in the making of accurate or reliable health determinations under same, similar, or differing sensor observation circumstances. Additionally, universal health metrics monitors' tools, methodologies, or programming are configurable for being easily diagnosed, repaired, or operationally altered if needed.

Universal health metrics monitors are configurable for utilizing their tools, methodologies, or programming in the making of selected determinations; wherein measure points that are used in the locating of selected analytically rich aspects, characteristics, or features are also utilized by universal health metrics monitors for establishing or maintaining the structure that is needed for consistently locating through utilization of measure points, selected analytically rich aspects, characteristics, or features of or from sensor observation-derived representations. Universal health metrics monitors' tools, methodologies, or programming are configurable for being utilized for operational purposes including (a) grouping measure points into standard target sets of measure points, (b) determining which analytically rich aspects, characteristics, or features of or from sensor observation-derived representations are to be located through utilization of measure points, (c) locating selected measure points on sensor observation-derived representations, (d) assigning appropriate informational representations to selected analytically rich aspects, characteristics, or features of or from sensor observation-derived representations, (e) storing selected informational representations in datasets, (f) utilizing informational representations from datasets in the making of selected health determinations, or (g) for purposes from a complete spectrum of other operational purposes for which universal health metrics monitors' tools, methodologies, or programming can be utilized.

Universal health metrics monitors are configurable for achieving the highest attainable percentages of simplicity, efficiency, accuracy, or reliability through their utilization of selected measure points, standard target sets of measure points, datasets, concise datasets, and standard tools, methodologies, or programming in their providing of selected health determinations regarding people who are subjects of sensor observations.

In some instances, informational representations regarding selected analytically rich aspects, characteristics, or features of or from sensor observation-derived representations need to be intermittently or constantly updated with the most recent informational representations regarding (a) measure points, or (b) analytically rich aspects, characteristics, or features of or from sensor observation-derived representations. As an example, a person with very light-colored eyebrows, uses an eyebrow pencil several times a day to give their eyebrows a more distinct visual presence. Slight changes to the locations of the eyebrows occur each time the eyebrow pencil is applied. Universal health metrics monitors are configurable for making appropriate changes to selected informational representations regarding the measure points that are utilized in the locating of the person's eyebrows every time the person reapplies eyebrow pencil.

Universal health metrics monitors are further configurable for utilizing measure points in their making of selected determinations regarding or utilizing the measured locations or the measured orientations of selected analytically rich aspects, characteristics, or features of or from people who are subjects of sensor observations.

Examples of cyber determinations regarding the measured locations or the measured orientations of selected analytically rich aspects, characteristics, or features of or from sensor observation-derived representations include (a) measured locations or measured orientations of sensor observation-derived representation of scars on sensor observation-derived representations of people, (b) measured locations or measured orientations of sensor observation-derived representations of marks on sensor observation-derived representation of people, (c) measured locations or measured orientations of sensor observation-derived representations of tumors on sensor observation-derived representations of people, (d) measured locations or measured orientations of sensor observation-derived representations of wounds on sensor observation-derived representations of people, or (e) measured locations or measured orientations of analytically rich aspects, characteristics, or features of or from sensor observation-derived representations, from a complete spectrum of analytically rich aspects, characteristics, or features of or from sensor observation-derived representations of people.

Universal health metrics monitors are configurable for utilizing scalable configurable grids in their making of selected health determinations.

Using a video camera observations of a person's face as an example, universal health metrics monitors are configurable for comparing patterns of observed levels of red, green, or blue light at each of the pixels from within scalable configurable grids. In this example, scalable configurable grids are used to define areas of pixel-based sensor observation-derived representation where it is anticipated that the measure point that locates the tip of a person's nose will accurately or reliably be located. Patterns of observed levels of red, green, or blue light are analyzed utilizing tools, methodologies, or programming from a complete spectrum of tools, methodologies, or programming that are utilizable by universal health metrics monitors in their determining of where selected measure points will be located on the pixel grids of sensor observation-derived representations.

Scalable configurable grids can be square, rectangular, round, oval, or irregularly shaped.

Universal health metrics monitors are configurable for performing analysis of all or parts of the pixels from within scalable configurable grids.

Two or more pixels are present within each scalable configurable grid.

Scalable configurable grids utilize, scale to, or conform with the pixel grids of sensor observation-derived representations.

Measure points can be regularly located, for example, at 10, 50, or 100-pixel distances apart on both the X and the Y axes of pixel grids to form a plurality of groups of pixels from within a plurality of scalable configurable grids Groups of pixels can be a selected subject of analysis, wherein results from analysis are usable in whole or in part by universal health metrics monitors in their making of selected health determinations. Adjoining or overlapping scalable configurable grid-defined groups of pixels are combinable, wherein the combined groups can be utilized by universal health metrics monitors in their making of selected health determinations.

Scalable configurable grids are configurable for providing the structure that is needed for performing repeated analysis of the same specific selected areas of pixels from each comparable image sensor observation-derived representation that is used by universal health metrics monitors in their making of selected health determinations.

Additionally, analysis of what was observed from within scalable configurable grids can be performed at increasing or decreasing levels of detail as needed. Similarities or differences between informational representations from differently scaled scalable configurable grids can be utilized by universal health metrics monitors in their making of selected health determinations.

Universal health metrics monitors are configurable for utilizing tools, methodologies, or programming from a complete spectrum of tools, methodologies, or programming that can be utilized in their making of selected determinations regarding or utilizing groups of pixels. Universal health metrics monitors are also configurable for using tools, methodologies, or programming from a complete spectrum of tools, methodologies, or programming that can be utilized by universal health metrics monitors in their making of selected determinations regarding or utilizing groups of pixels that are located through utilization of one or more measure points.

Universal health metrics monitors' summation table tools, methodologies, or programming are utilizable in combination with scalable configurable grids in the making of selected predictions or determinations regarding where measure points will be located on current or on upcoming sequential sensor observation-derived representations. Summation tables are configurable for utilizing scalable configurable grids as the structures that aid in their accurate or reliable locating of the same aspects, characteristics, or features from every comparable image sensor observation-derived representation.

Summation table analysis is configurable for utilizing the sums of the observed levels of red, green, or blue light from all or parts of columns or rows of scalable configurable grids, wherein universal health metrics monitors use sums from summation analysis in their making of selected health determinations.

The sums of measured levels of red, green, or blue light that were observed from all or parts of columns or rows from pixel grids can be determined and utilized by universal health metrics monitors in their making of selected health determinations. Additionally, any combinations of sums from all or parts of columns or rows from within scalable configurable grids are utilizable for purposes from a complete spectrum of purposes for which sums of measurements of observed levels of red, green, or blue light from columns or rows from within scalable configurable grids can be utilized. One such utilization is the efficient locating of one specific person's face from video-formatted image sensor observation-derived representations.

Universal health metrics monitors are configurable for utilizing summation table analysis for determining how many pixels that selected aspects, characteristics, or features have moved from their relative locations in previous sequential sensor observation-derived representations.

Prior art facial recognition processes or procedures dedicate the largest percentage of their processing to finding faces. Universal health metrics monitors are configurable for comparing second-series observation summation table analysis of a person's face to first-series observation summation table analysis of a person's face, wherein universal health metrics monitors utilize informational representations from first-series observation summation table analysis of a person's face in their efficient locating of the same person's face from second-series observations.

Utilizing informational representations from summation table analysis of any one specific person in the finding of that specific person's face from video-formatted image sensor observation-derived representations will result in profound increases in operational efficiencies over prior art. Further, the same summation table-derived informational representations are usable as an initial cyber test of any one specific person's identity. Should it not be possible to use first-series summation table informational representations to find the face of a specific first-series observation subject from second-series observation-derived representations, then the second-series observation subject is unlikely to be the person from the first-series observations that they claim to be.

Universal health metrics monitors are configurable for accurately or reliably determining that the center of a measure point will be located, for example, one-half of a pixel up and one-third of a pixel to the right on the pixel grid of the next sequential sensor observation-derived representation. Movement of fraction of a pixel per image can be determined through utilization of the universal health metrics monitor's tools, methodologies, or programming that perform smudge analysis. Universal health metrics monitors are configurable for performing analysis of patterns of smudges from image sensor observation-derived representations in which analysis of measured levels of red, green, or blue light or any other colors of light from a complete spectra of colors of light that can be utilized for accurately or reliably (a) indicating the presence of remnants of light that were fully present prior to the exact point in time that an image was captured, or (b) utilizing light from adjoining areas that has reflected or refracted upon specific pixels or specific areas of pixels. Universal health metrics monitors are configurable for utilizing analysis of observed presences of remnants of light, reflected light, or refracted light in their making of determinations from a complete spectrum of health determinations regarding people who are subjects of sensor observations where remnants of light, reflected light, or refracted light are observed.

When viewing a piece of black electric tape that is affixed to a piece of white paper, one might assume that the color of the pixels at the precise edge where the black tape and the white paper adjoin would be black on the tape side and white on the paper side. However, sensors that are used to capture images of the tape and paper do not capture images with those results. Light from the black, and light from the white impose on each other where black and white adjoin. The imposing of colored light from one pixel to another is due, at least in part, to the reflective or refractive properties of light. The highest level of the imposition occurs at the edge where the black and the white meet as evidenced by the color values for the black, which are lightest at the point where the two colors meet, and the color values for the white, which are darkest at the point where the two colors meet. If an image sensor and the paper and tape are stationary while the image is being captured, then there will usually be a clean gradation of or mixing of color where black meets white. Should there be no movement of the sensor or the tape and paper, then analysis of the point where tape and paper adjoin will result in an evenly gradated change of color from each sequential image. Should there be movement of the image sensor or the tape and paper when the sensor observation is captured, then a smudge or smudges in the gradated colors, or an elongation of the gradated colors is reliably observed. The smudge or smudges can be used by universal health metrics monitors for purposes from a complete spectrum of purposes for which smudges from sensor observation-derived representations can be utilized. One such utilization would be to predict directions and distances of movement from a current image's pixel grid to the next sequential image's pixel grid.

Another utilization of smudge analysis is for determining the distance and the direction of movement that occurs from one sensor observation-derived representation to the next sequential representation when observed movement between images is less than one pixel in distance. Through utilization of smudge analysis, the amount that any of the colors of observed light from one pixel infringe or impose on differently colored light from adjoining pixels is usable by universal health metrics monitors in their making of selected determinations regarding the distance or direction of movement, in fractions of a pixel, that selected analytically rich aspects, characteristics, or features have moved on a pixel grid since the previous sensor observation-derived representation.

Through utilization of the security, safety, and privacy that is enabled by the identity tests of the universal health metrics monitors, it will be possible to provide all or part of a person's own personal and private health information to health care practitioners of choice securely and privately. Doing so should enable the practitioners to provide the person with the best possible health care treatments or outcomes.

It will also be possible for a person to anonymously provide all or part of their health records to selected others for use in health-related research.

Utilizing a bicorder/health metrics monitor, each person can enjoy the benefits of secure and private uninterrupted observations and analysis of any number of measures of their health.

When the world was experiencing the initial ravages of COVID-19 the pandemic resulted in lost jobs, lost revenues, failed businesses, and financially devastated lives. Perhaps widespread use of universal health metrics monitors that were configured to be used in whole or part as COVID-19 monitors or as sensor observation-derived COVID-19 tests, could have enabled far better control of the virus's initial spread and lessened unwanted consequences.

Universal health metrics monitors can constantly monitor a person's stream of health sensor data for known health metrics or health metrics patterns that are reliable indicators of (a) an onset of an adverse health occurrence, (b) adverse health occurrences that are occurring, (c) adverse health occurrences that have occurred, (d) intermediate stages a person's cycles of adverse health occurrences, (e) when a person is no longer contagious, or (f) the end of a person's adverse health occurrence.

Universal health metrics monitors disclosed herein are configurable for being utilized as continuous, real-time, 24/7 monitors that reliably detect a person is infected with COVID-19, preferably before the infected person is contagious. Instantaneous real-time alerts from universal health metrics monitors would enable infected people to contact health care providers and self-quarantine right away, thereby significantly limiting or stopping spread of the virus.

Universal health metrics monitors can be further configured to monitor a person's health through the entire cycle of their infection. Universal health metrics monitors can also be configured to make reports that infected people are no longer contagious. Early knowledge that people are infected, along with knowledge of exactly where people are in their cycle of infection, would be valuable tools in providing the best possible health-related treatments and outcomes.

Knowing a person is no longer contagious would allow that person to end quarantine and safely go back to their usual life. In addition, all those who were not found to be infected with the virus could safely go about their lives with the security of knowing they will be instantly alerted should their universal health metrics monitors detect they are infected with COVID-19. Allowing those who are not infected or those who were infected but were no longer contagious to safely go about their regular lives would be far better than the methodologies that have been used.

Universal health metrics monitors are configurable for monitoring intermittent or continuous streams of sensor data for changes in health metrics data that only occur with people who are known to be infected with COVID-19. Once these are discovered, the changes (tells) from the streams of health sensor data can then be utilized to determine the need to alert the person that they have a COVID-19 infection. In addition, this same simple methodology can be utilized to provide infected people with interactive alerts at various stages in the cycle of their COVID-19 infections.

Figure 2:
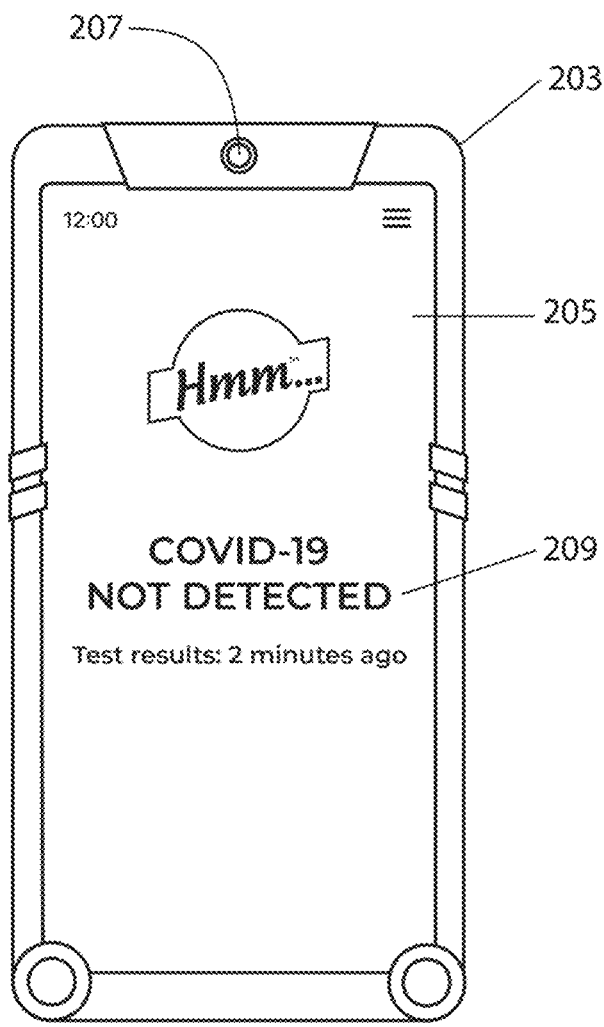
FIG. 2 is an illustration of a particular non-limiting embodiment of a hand held pocket sized universal health metrics monitor showing the results of a COVID-19 test, that the health metrics monitor just made, on its display screen.

The foregoing principles are further appreciated with respect to FIG. 2, which illustrates a first particular, non-limiting embodiment of utilization of a universal health metrics monitor in accordance with the teachings herein. As seen therein is a hand-held pocket-sized health metrics monitor 203, equipped with an image display screen 205, and a video-formatted image sensor 207. The health metrics monitor 203, has completed a one-time COVID-19 test and the results of the test and the duration of time since the test was taken 209, are shown on the image display screen 205. The results of the one-time COVID-19 test can be used for any purpose from a full spectrum of purposes COVID-19 test results can be utilized.

Examples of sensor-observable occurrences that could be reliable indicators that a person is infected with COVID-19 include (a) patterns of movement from coughing or shivering, (b) changes in body temperature, (c) patterns of changes in body temperature, (d) changes in average blood oxygen levels, (e) changes in patterns of blood oxygen levels, (f) changes in patterns of respiration, (g) changes in patterns of blood oxygenation levels during respiration, (h) changes in average blood oxygenation levels, (i) changes in patterns of blood oxygenation levels, (j) the presence of odors or chemical signatures that only occur during COVID-19 infections, (k) facial affect, (l) the sounds of respiratory abnormalities, or (m) combinations thereof.

The same processes or procedures that were used for discovering the sensor-observable tells of a COVID-19 infection can also be used by the universal health metrics monitors for discovering sensor-observable tells for any other adverse health issue from a complete spectrum of sensor-observable adverse health issues.

As one non-limiting example of use, data streams from odor or chemical sensors are utilized by universal health metrics monitors for identifying and then reporting on an observed presence of specific odors or chemical signatures that reliably indicate a person has an abnormal cancer cell count. Use of intermittent or constant monitoring for the earliest sensor-detectable specific odors or chemical signatures that reliably indicate an abnormal cancer cell count has occurred may be the key to ending cancer-related illness.

Prior art in the field of healthcare typically utilizes one-time analysis or testing of a person for making health-related determinations or diagnoses. Universal health metrics monitors introduce and enable the use of intermittent or continuous 24/7 monitoring or recording of a person's health metrics. If knowledge is power, then the knowledge that will be gained by the continuous monitoring or recording of people's health metrics may well be the catalyst for the most profound healthcare advancement we will see. One of the advancements will be the discovery of tells that reliably indicate adverse health issues have occurred or will soon occur. The tells will be found by determining what all people who have had the adverse health occurrence have in common concerning changes or changes in patterns of their health metrics data that only occur with a common adverse health occurrence. As an example, should everyone who has a heart attack or stroke experience the same changes or patterns of changes in their health metrics three days or three hours prior to their adverse health occurrence, then universal health metrics monitors can be configured to monitor a person's stream of health metrics data for the specific changes or patterns of changes that reliably indicate a person will have a heart attack or stroke, and alert the person when the reliable indicators are observed.

Using a previous example, sensor-detectable odors or chemical signatures may soon be used to reliably indicate a person has an abnormal cancer cell count. Some portion of the people who have the onset of this sensor-observed adverse health occurrence will find that it does not persist and quickly goes away. It is possible that commonalities exist between the members of this group. This discovery could lead to an effective treatment when they are notified by their health metrics monitor that an abnormal cancer cell count has been observed. This concept for discovering cures is universally usable for any adverse health occurrences that have been detected by universal health metrics monitors and then can no longer be detected without prescribed intervention.

Another example of the power that knowledge from use of universal health metrics monitors will enable is maintaining optimal health metrics. At present little is known about optimal health metrics or how to maintain optimal health metrics throughout a person's lifetime. Additionally, very little is known about the effects that having less than optimal health metrics plays in our mental or physical health or well-being. Universal health metrics monitors are configurable for helping a person achieve and maintain optimal health metrics for the remainder of their life. Optimal health metrics will be unique to each person and the universal health metrics monitors disclosed herein are configurable for being utilized as personalized tools that will enable people to achieve any attainable level of optimal health metrics through activity or management of their intake of food, drink, medication, or supplements.

Use of changes or patterns of changes in health metrics data that occur over time is a very powerful tool that will enable vast improvements in health care methodologies. However, use of changes or patterns of changes is not the only methodology that universal health metrics monitors can utilize for detecting selected adverse health issues. Universal health metrics monitors are also configurable for making selected sensor observation-enabled health-related determinations using data that was derived at one time (one-time tests). Preferably this type of determination will be made based upon one or more one-time sensor-observations that reliably indicate a selected adverse health-related occurrence has been observed. As an example, dogs are now used to detect that people have abnormal cancer cell counts or that people are infected with COVID-19. Universal health metrics monitors are configurable for utilizing sensor observation data to identify odors or chemical signatures that reliably indicate that people have abnormal cancer cell counts or that people are infected with COVID-19.

Universal health metrics monitors are configurable for providing one-time tests regarding any sensor-observable aspects, characteristics, or features of people's health from a complete spectrum of one-time, sensor-observable, analytically rich aspects, characteristics, or features of people's health. This capability will profoundly change how adverse health occurrences are diagnosed either remotely or in person.

We live in a technologically interconnected world with vast cyber resources. This colossal spectrum of available cyber resources is ever widening, and over time our technologically interconnected world appears to be destined to provide every possible cyber resource that humanity could ever want or need. When that time comes, the entire body of cyber resources will include and rely heavily upon scalable, configurable, complete spectrum universal health metrics monitors (such as the scalable, configurable, complete spectrum universal health metrics monitors disclosed herein) that are configurable for utilizing measure points in their locating of selected analytically rich aspects, characteristics, or features of or from sensor-observation-derived representations, datasets, or concise datasets in their making of selected health determinations regarding any one specific person, and also every other health determination that our world could ever want or need regarding people who are subjects of sensor observations.

One skilled in the art will appreciate that some of the methodologies disclosed herein can be implemented utilizing software programs. Such software programs can take the form of suitable programming instructions disposed in tangible, non-transient medium which, when implemented by computer processors, performs all or parts of the methodologies described herein.

While the disclosed universal health metrics monitors have been defined in terms of their preferred and alternative embodiments, those of ordinary skill in the art will understand that numerous other embodiments and applications of the disclosed universal health metrics monitors will become apparent. Such other embodiments and applications shall be included within the scope and meaning of the disclosure as defined by the appended claims. Moreover, it is to be understood that the above description of the present disclosure is illustrative and is not intended to be limiting. It will thus be appreciated that various additions, substitutions, and modifications may be made to the above-described embodiments without departing from the scope of the present disclosure. Accordingly, the scope of the present disclosure should be construed in reference to the appended claims.

What is claimed is:

1. As calable, configurable, complete spectrum, universal health metrics monitoring system comprising:
    universal health metrics monitors comprising program instructions stored in a memory of the scalable, configurable, complete spectrum, universal health metrics monitoring system and executable to:
        utilize resources that include computing devices, bicorders, tools, methodologies, programming, information, selected criteria, sensors and data to capture, record, monitor, or report on at least a portion of sensor observations of analytically rich aspects, characteristics, or features of people's health, wherein the sensors include at least one of internal sensors, external sensors, wearable sensors, sensors that are in an observable proximity of people who are subjects of sensor observations, or other sensors that are utilizable in making of selected determinations regarding or utilizing sensor observations of people's health, wherein the bicorders include at least one of a virtual device, a physical device, or a combination of a physical device and a virtual device, wherein the computing devices include at least one of a virtual device, a physical device, or a combination of a physical device and a virtual device, wherein a physical computing device includes a tangible non-transient memory device and one or more of an input device or an output device;
        make or report on selected health determinations regarding or utilizing sensor-observed analytically rich aspects, characteristics, or features of people's health;
        make or report on determinations that identify health-related tells; said health-related tells regarding or utilizing analytically rich aspects, characteristics, or features of or from sensor observation-derived representations of people; wherein the health-related tells are utilized in identification of health-related occurrences that a person has had or will have;
        select or derive data that are included in datasets or concise datasets, wherein the concise datasets include selected sensor data or derived data, wherein selected data include informational representations that were selected from sensor observation datasets, and wherein derived data include informational representations that were derived from processing informational representations that were selected from sensor observation datasets or informational representations that were selected from derived data;
        utilize datasets or concise datasets in determinations regarding people's health;
        process the derived data via utilization of; selected tools, methodologies, or programming;
        locate selected analytically rich aspects, characteristics, or features of or from sensor observations or sensor observation-derived representations of people via utilization of measure points;
        assign appropriate informational representations to said measure points and to said selected analytically rich aspects, characteristics, or features of or from said sensor observation-derived representations that are located through utilization of said measure points;
        identify tells that are utilizable to make determinations regarding people's health;
        make one-time single event determinations regarding or utilizing sensor observations, people's health, or measure points, intermittently provided determinations regarding or utilizing sensor observations, people's health, or measure points, or constantly provided determinations regarding or utilizing sensor observations, people's health, or measure points, wherein the sensor observations are
    from points in time or over periods of time; and
    perform, at least one part of at least one operation from a group consisting of:
        (a) first-series sensor observation operations, wherein the first-series sensor observations or people who are subjects of the first-series sensor observations have previously determined analytically rich aspects, characteristics, or features, wherein the health metrics monitors are further configured to:
            recognize said previously determined aspects, characteristics, or features;
            assign appropriate informational representations regarding said recognized aspects, characteristics, or features of or from said sensor observations or said people; and
            utilize said assigned informational representations to make selected determinations regarding or utilizing said sensor observations or said people's health;
        (b) second-series sensor observation operations, wherein the second-series sensor observations or people who are subjects of the second-series sensor observations have selected yet-to-be-determined analytically rich aspects, characteristics, or features, wherein the health metrics monitors are further configured to:
            recognize the yet-to-be-determined analytically rich aspects, characteristics, or features;

assign appropriate informational representations regarding the analytically rich aspects, characteristics, or features of or from said sensor observations or said people; and utilize the assigned informational representations to make selected determinations regarding or utilizing said sensor observations or said people's health;

(c) measure point operations, wherein the health metrics monitors are further configured to:

utilize measure points in locating the selected analytically rich aspects, characteristics, or features of or from sensor observation-derived representations of sensor observations or people who are subjects of sensor observations;

assign appropriate informational representations regarding said measure points or said selected analytically rich aspects, characteristics, or features; and store or utilize the informational representations when making the selected determinations regarding or utilizing said sensor observations or said people's health, (d) concise datasets operations, wherein the health metrics monitors are further configured to select, derive, or utilize data for or from concise datasets, wherein said concise datasets include selected sensor data or derived data, wherein said selected sensor data includes informational representations from sensor observation datasets, and wherein said derived data is comprised of informational representations that were derived from (i) processing of selected informational representation from said sensor observation data, or (ii) processing of selected informational representations from said derived data, wherein informational representations from said selected sensor data or said derived data are utilizable by said health metrics monitors in their making of selected determinations regarding or utilizing said sensor observations or said people's health;

(e) matching operations, wherein the health metrics monitors are further configured to match selected informational representations from second-series observations to comparable informational representations from first-series observations;

(f) comparing operations, wherein the health metrics monitors are further configured to make comparisons of selected informational representations from second-series observations to selected informational representations from first-series observations, wherein said health metrics monitors utilize data from said comparisons (i) for providing conclusions, or (ii) in their making of said selected health determinations;

(g) determining operations, wherein the health metrics monitors are further configured to utilize said conclusions from said comparing operations or said information in their making of selected determinations regarding or utilizing said sensor observations or said people's health; and (h) reporting operations, wherein the health metrics monitors are further configured to make selected reports regarding or utilizing aspects, characteristics, or features of or from their operations.

2. The scalable, configurable, complete spectrum, universal health metrics monitoring system of claim 1, wherein said universal health metrics monitors are further configurable for utilizing (a) tools, (b) methodologies, (c) programming, (d) people, or (e) combinations thereof for selecting aspects, characteristics, or features of or for their operations; said tools, methodologies, and programming are from a complete spectrum of tools, methodologies, and programming that can be utilized for selecting aspects, characteristics, or features of or for operations of said universal health metrics monitors.

3. The scalable, configurable, complete spectrum, universal health metrics monitoring system of claim 1, wherein said universal health metrics monitors are further configurable for utilizing at least one member selected from a group consisting of (a) tools, (b) methodologies, (c) programming, (d) data, (e) information, (f) people, and (g) combinations thereof in their making of determinations regarding points where selected measure points will be located on sensor observation-derived representations; and wherein at least one member selected from a group consisting of said (a) tools, (b) methodologies, (c) programming, (d) data, (e) information, (f) people, and (g) combinations thereof are utilized for making at least one type of determination selected from a group consisting of (i) determinations of where selected measure points will be located on sensor observation-derived representations of specific aspects, characteristics, or features of any one specific person who is a subject of a sensor observation, (ii) determinations of where selected measure points will be located on sensor observation-derived representations of specific aspects, characteristics, or features of people who are sensor observations subjects that are members of specific groups of people, and (iii) determinations of where selected measure points will be located on sensor observation-derived representations of specific aspects, characteristics, or features of people that are sensor observation subjects who are from a complete spectrum of people who are sensor observation subjects.

4. The scalable, configurable, complete spectrum, universal health metrics monitoring system of claim 1, wherein analytically rich aspects, characteristics, or features of said people who are subjects of sensor observations include aspects, characteristics, or features from a complete spectrum of sensor-observable analytically rich aspects, characteristics, or features of people;

wherein measure points are utilizable in locating selected analytically rich aspects, characteristics, or features of or from sensor observation-derived representations of people;

said measure points are utilizable for purposes from a complete spectrum of purposes for which measure points that are utilized in locating selected analytically rich aspects, characteristics, or features of or from sensor observation-derived representations of people can be utilized;

said spectrum of analytically rich aspects, characteristics, or features of or from sensor observation-derived representations of people includes sensor observation-derived representations of (a) scars, (b) marks, (c) wounds, (d) fingerprint features, (e) axis points at joints, (f) tips of noses, (g) corners of eyes, (h) centers of pupils, (i) corners of mouths, (j) tips of fingers, (k) patterns of sweat glands, (l) coughs, (m) tremors, (n)

shivers, (o) voices, (p) pulses, (q) blood pressure, (r) blood oxygen saturation, (s) rapid eye movement patterns, or (t) respiration.

5. The scalable, configurable, complete spectrum, universal health metrics monitoring system of claim 1,
wherein said universal health metrics monitors are further configurable for making selected determinations regarding or utilizing said sensor observations or said people who are subjects of said sensor observations; wherein said sensor observations are made (a) at points in time, or (b) over periods of time; and said universal health metrics monitors include, in datasets, informational representations regarding or utilizing selected analytically rich changes that occur over time to sensor-observable aspects, characteristics, or features of or from sensor observation-derived representations of said subjects of said sensor observations; wherein said analytically rich changes that occur over time to people who are subjects of sensor observations include changes to analytically rich aspects, characteristics, or features of sensor observation-derived representations of people's (a) heads, (b) faces, (c) mouths, (d) eyes, (e) eyebrows, (f) noses, (g) arms, (h) hands, (i) fingers, (j) legs, (k) feet, (l) necks, (m) torsos, (n) skin, (o) hearts, (p) stomachs, (q) intestines, (r) livers, (s) kidneys, (t) lungs, (u) breath, (v) vascular systems, (w) brains, (x) spinal cords, (y) neural systems, (z) neural activities, (aa) digestive systems, (bb) digestive activities, (cc) skeletons, (dd) blood, (ee) odors, (ff) voices, (gg) movements, (hh) tips of noses, (ii) corners of eyes, (jj) centers of pupils, (kk) axis points at joints, (ll) patterns of blood oxygenation during respiration cycles, (mm) presence of chemical compounds, (nn) presence of odors, or (oo) analytically rich aspects, characteristics, or features of sensor observation-derived representations of people from a complete spectrum of other aspects, characteristics, or features of sensor observation-derived representations of people where sensor-observable analytically rich changes occur over time.

6. The scalable, configurable, complete spectrum, universal health metrics monitoring system of claim 1,
wherein said universal health metrics monitors are further configurable for making selected determinations that are utilized in processes of accurately or reliably granting or denying people or cyber devices access to at least one member selected from a group consisting of (a) all or parts of said universal health metrics monitors or bicorders, (b) all or parts of resources that are being utilized by said universal health metrics monitors or bicorders, and (c) all or parts of resources that are utilizing said universal health metrics monitors or bicorders.

7. The scalable, configurable, complete spectrum, universal health metrics monitoring system of claim 6,
wherein said universal health metrics monitors are further configurable for being utilized for accurately or reliably performing testing of identities of specific people; wherein universal health metrics monitors' identity testing can be configured to utilize selected levels of participation by people who are subjects of said identity testing; and wherein said selected levels of participation range from tested people being observable by sensors, but not consciously engaged in said testing; to said tested people being observable and consciously engaged participants in said testing.

8. The scalable, configurable, complete spectrum, universal health metrics monitoring system of claim 1,
wherein said universal health metrics monitors are configurable for being utilized for making selected one-time single-event test determinations regarding or utilizing selected sensor-observed analytically rich aspects, characteristics, or features of people's health;
said selected one-time single-event test determinations are configurable for being made or utilized in real time or at times thereafter;
said selected one-time single-event test determinations are made utilizing data from a complete spectrum of data that can be utilized by said universal health metrics monitors in their making of one-time single-event test determinations regarding or utilizing selected sensor-observed analytically rich aspects, characteristics, or features of people's health;
selected analytically rich aspects, characteristics, or features of people's health are from a complete spectrum of sensor-observable analytically rich aspects, characteristics, or features of people's health;
a complete spectrum of one-time single-event test determinations regarding or utilizing selected sensor-observable analytically rich aspects, characteristics, or features of people's health includes test determinations regarding a presence of (a) COVID-19, (b) H1N1, (c) Ebola, (d) cancer, or (e) a complete spectrum of other aspects, characteristics, or features of people's health that can be sensor-observed, tested, and accurately or reliably reported on;
said one-time single-event test determinations regarding or utilizing selected sensor-observed analytically rich aspects, characteristics, or features of people's health can be utilized for purposes from a complete spectrum of purposes for which one-time single-event test determinations regarding or utilizing sensor-observed analytically rich aspects, characteristics, or features of people's health can be utilized;
said complete spectrum of purposes for which said one-time single-event test determinations can be utilized includes making test determinations regarding or utilizing sensor-observed analytically rich aspects, characteristics, or features of people's health prior to or immediately prior to tested people being granted or denied access to at least one member selected from a group consisting of (i) schools, (ii) public transportation, (iii) houses of worship, (iv) workplaces, (v) events, (vi) sporting activities, (vii) restaurants, (viii) bars, (ix) stores, (x) hospitals, (xi) parks, (xii) prisons, (xiii) nursing homes, (xiv) grocery stores, (xv) theaters, (xvi) gyms, (xvii) health care providers' offices, (xviii) concerts, (xix) salons, (xx) meat processing plants, and (xxi) other places or activities where it is required or desired to determine if tested people do or do not have selected aspects, characteristics, or features of their health that would or should exclude specific tested people from gaining access to those places or activities.

9. The scalable, configurable, complete spectrum, universal health metrics monitoring system of claim 1,
wherein said universal health metrics monitors are further configurable for utilizing measure points in their locating of sensor observation-derived representations of selected analytically rich aspects, characteristics, or features of or from sensor observation-derived representations of people's faces;
said measure points are utilized for purposes from a complete spectrum of purposes for which measure points that are utilized in locating selected analytically rich aspects, characteristics, or features of or from sensor observation-derived representations of people's faces of can be utilized;

said complete spectrum of purposes for which measure points that are used in locating selected analytically rich aspects, characteristics or features of or from sensor observation-derived representations of people's faces can be utilized includes (a) determining identities of yet-to-be-identified people, (b) authenticating claimed identities of yet-to-be-identified people, (c) determining people's facial affects, (d) determining people's facial expressions, (e) determining gaze of people's eyes, (f) determining sensor or camera angles, (g) determining sensor observation lighting circumstances, (h) determining people's poses, (i) determining what portions of people's faces are being observed, (j) determining measures of people's state of mental or physical health, (k) determining people's pulse rates, (l) determining people's blood pressure, (m) determining relationships between sensors and measure points that are located on sensor observation-derived representations of people's faces, (n) identifying occurrences of micro-expressions, and (o) making determinations from a complete spectrum of other determinations for which measure points used in locating selected analytically rich aspects, characteristics, or features of or from sensor observation-derived representations of people's faces can be utilized.

10. The scalable, configurable, complete spectrum, universal health metrics monitoring system of claim 1,
wherein said universal health metrics monitors are further configurable for making selected determinations regarding or utilizing differences between sensor observation-derived representations that are captured at an exact time that increased blood flow from a heartbeat is at or near its highest level, and sensor observation-derived representations that are captured at a lower level of blood flow, including a lowest level of blood flow; said changes can be used for making determinations regarding a person's health that cannot be made using only one of said sensor observation-derived representations;
wherein said determinations are from a complete spectrum of health determinations that can be made regarding or utilizing differences between sensor observation-derived representations that are captured at or near a time that increased blood flow from a heartbeat is at its highest level, and sensor observation-derived representations that are captured at a lower level of blood flow, including a lowest level of blood flow.

11. The scalable, configurable, complete spectrum, universal health metrics monitoring system of claim 1,
wherein said universal health metrics monitors are further configurable for making selected determinations regarding or utilizing measured locations of or measured orientations of selected analytically rich aspects, characteristics, or features of or from sensor observation-derived representations of people;
said analytically rich aspects, characteristics, or features of or from said people are from a complete spectrum of sensor observation-derived representations of analytically rich aspects, characteristics, or features of or from people;
measured locations of or measured orientations of said selected analytically rich aspects, characteristics, or features of or from said sensor observation-derived representations of said people include measured locations of or measured orientations of (a) sensor observation-derived representations of micro-expressions on sensor observation-derived representation of people's faces, (b) sensor observation-derived representations of external wounds on sensor observation-derived representations of people, (c) sensor observation-derived representations of orientations of people's joints on sensor observation-derived representations of people, (d) sensor observation-derived representations of skin or tissue irregularities on sensor observation-derived representations of people, (e) sensor observation-derived representations of axis points at joints on sensor observation-derived representations of people, (f) sensor observation-derived representations of pulse points on sensor observation-derived representations of people, or (g) sensor observation-derived representations of analytically rich aspects, characteristics, or features of people from a complete spectrum of other sensor observation-derived representations of analytically rich aspects, characteristics, or features of people.

12. The scalable, configurable, complete spectrum, universal health metrics monitoring system of claim 1,
wherein said universal health metrics monitors are further configurable for utilizing measure points in their locating of sensor observation-derived representations of one or more tips of people's fingers;
said measure points are utilized for purposes from a complete spectrum of purposes for which measure points that are utilized in locating sensor observation-derived representations of people's fingertips can be used;
said complete spectrum of purposes includes utilization of said measure points as components of fingertip-to-cyber device touchless user interfaces; and
said cyber devices are types of cyber devices from a complete spectrum of types of cyber devices that can utilize fingertip-to-cyber device touchless user interfaces.

13. The scalable, configurable, complete spectrum, universal health metrics monitoring system of claim 1,
wherein said universal health metrics monitors are further configurable for utilizing measure points in their locating of axis points from sensor observation-derived representations of joints of people;
said measure points that locate said axis points are utilized for purposes from a complete spectrum of purposes for which measure points that locate sensor observation-derived representations of axis points of people's joints can be utilized; and
said complete spectrum of purposes for which measure points that are utilized in locating sensor observation-derived representations of axis points of joints of people can be utilized includes (a) making selected determinations regarding or utilizing observed geometries of said sensor observation-derived representation of said joints of people, or (b) making selected determinations that utilize said measure points that locate said sensor observation-derived representations of said axis points of said joints of said people for purposes from a complete spectrum of other purposes for which measure points that locate sensor observation-derived representations of axis points of joints of people can be utilized.

14. The scalable, configurable, complete spectrum, universal health metrics monitoring system of claim 1,
wherein said universal health metrics monitors are further configurable for being utilized for making selected determinations regarding or utilizing analytically rich aspects, characteristics, or features of observed geometries of sensor observation-derived representation of joints of people; and said selected analytically rich aspects, characteristics, or features of geometries of said sensor observation-derived representations of joints of people are utilized for purposes from a complete spectrum of purposes for which analytically rich aspects, characteristics, or features of observed geometries of sensor observation-derived representations of joints of people can be utilized.

15. The scalable, configurable, complete spectrum, universal health metrics monitoring system of claim 1, wherein said universal health metrics monitors use measure points in their making of selected measurements;

said selected measurements are from a complete spectrum of measurements that can be made through use of measure points that are utilized in locating selected analytically rich aspects, characteristics, or features of or from sensor observation-derived representations; and said complete spectrum of measurements that can be made through use of said measures points includes (a) measured distances between measure points, (b) measured angles where lines between measure points meet or intersect, (c) measured locations of measure points, aspects, characteristics, or features, (d) measured orientations of measure points, aspects, characteristics, or features, (e) measured relationships between measure points, aspects, characteristics, or features, (f) time of capture of sensor observations or parts thereof, (g) measured pressures at or in areas of measure points, (h) measured temperatures at or in areas of measure points, (i) measured levels of colored light at or in areas of measure points, (j) measured grayscale levels at or in areas of measure points, (k) measured odors at or in areas of measure points, (l) measured chemical presences at or in areas of measure points, (m) measured sound at or in areas of measure points, or (p) measures of sensor-observable analytically rich aspects, characteristics, or features from a complete spectrum of other measurable sensor-observable analytically rich aspects, characteristics, or features of or from sensor observation-derived representations that can be located or reported on through utilization of measure points.

16. The scalable, configurable, complete spectrum, universal health metrics monitoring system of claim 1, wherein said universal health metrics monitors or bicorders are configurable for performing their operations, or parts thereof, in any usable order or sequence.

17. The scalable, configurable, complete spectrum, universal health metrics monitoring system of claim 1, wherein said universal health metrics monitors are further configurable for achieving selected attainable level of accuracy goals for selected determinations and said attainable level of accuracy goals fall in a range extending from 0% accuracy, and goes up to and includes 100% accuracy.

18. The scalable, configurable, complete spectrum, universal health metrics monitoring system of claim 1, wherein said universal health metrics monitors are further configurable for utilizing information or informational representations from sources that are not first-series observation operations or second-series observation operations.

19. The scalable, configurable, complete spectrum, universal health metrics monitoring system of claim 1, wherein said universal health metrics monitors or bicorders are further configurable for manipulating in possible ways operations of universal health metrics monitors, bicorders, health metrics monitor utilized resources, or, bicorders-utilized resources; said manipulating provides said universal health metrics monitors, bicorders, health metrics monitor utilized resources, or, bicorder utilized resources with selections of possible utilizations; said manipulating is utilized for purposes from a complete spectrum of purposes for which said manipulating can be utilized; said complete spectrum of purposes for utilizing said manipulating includes a purpose of aiding said universal health metrics monitors or bicorders in their operations or making said selected health determinations.

20. The scalable, configurable, complete spectrum, universal health metrics monitoring system of claim 1, wherein all or part of sensor observation datasets from sources that are not first-series observation operations are included as all or part of first-series observation datasets, and all or part of sensor observation datasets from sources that are not second-series observation operations are included as all or part of second-series observation datasets.

21. The scalable, configurable, complete spectrum, universal health metrics monitoring system of claim 1, wherein said universal health metrics monitors are further configurable for including health metrics monitor history; wherein said health metrics monitor history is comprised of health metrics monitor history records; and said health metrics monitor history records are utilizable for purposes from a complete spectrum of purposes for which health metrics monitor history records can be utilized.

22. A system comprising one or more universal health metrics monitors, wherein said universal health metrics monitors comprise program instructions stored in a memory and executable to or utilize tools, methodologies, programming, computers, sensor data, bicorders, and other necessary resources, all or part of which may be utilized in capturing, selecting, deriving, or utilizing data for or from datasets, said universal health metrics monitors utilize said data for or from said datasets in their making of selected determinations regarding or utilizing sensor observations or people's health; said universal health metrics monitors further comprise deriving or utilizing information from points in time or from periods of time, from a complete spectrum of information that includes information regarding observed analytically rich aspects, characteristics, or features of or from sensor observations or people, thereby obtaining sensor-derived information;

said sensor observations are types of sensor observations from a group consisting of (a) visual sensor observations, (b) audible sensor observations, (c) thermal sensor observations, (d) olfactory sensor observations, (e) tactile sensor observations, (f) chemical sensor observations, or (g) types of sensor observations, from a complete spectrum of other types of sensor observations that can be utilized by said universal health metrics monitors;

said universal health metrics monitors are configurable for capturing, selecting, deriving, or utilizing data for or from datasets or concise datasets, or making selected health determinations through utilization of at least one member from a list consisting of (a) tools, (b) methodologies, (c) programming, (d) computers, (e) bicorders, (f) sensor data, (g) said information, (h) criteria that are utilized by said universal health metrics monitors, and (i) other necessary resources;

said universal health metrics monitors make at least one type of health determination selected from a group consisting of (i) one-time, single-event health determinations, (ii) intermittently made health determinations, and (iii) constantly made health determinations;

said selected health determinations are utilized for purposes from a complete spectrum of purposes for which health determinations regarding or utilizing sensor observations or the health of people who are subjects of sensor observations can be utilized; and said universal health metrics monitors further comprise utilizing at least one part of at least one operation selected from a group consisting of (a) first-series observation operations, wherein said universal health metrics monitors utilize sensor observations, wherein said sensor observations or people who are subjects of said sensor observations have previously determined analytically rich aspects, characteristics, or features, said universal health metrics monitors recognize said aspects, characteristics, or features, said recognized aspects, characteristics, or features are utilizable by said universal health metrics monitors in their making of selected health determinations, said universal health metrics monitors assign appropriate informational representations regarding selected known analytically rich aspects, characteristics, or features of said sensor observations or said people who are subjects of said sensor observations, said universal health metrics monitors include all or part of said informational representations in first-series observation datasets, (b) second-series observation operations, wherein said universal health metrics monitors utilize sensor observations, and wherein said sensor observations or people who are subjects of said sensor observations have selected yet-to-be-determined analytically rich aspects, characteristics, or features, said universal health metrics monitors recognize said selected yet-to-be-determined aspects, characteristics, or features, said universal health metrics monitors assign appropriate informational representations regarding any selected and now determined analytically rich aspects, characteristics, or features of said sensor observations or said people who are subjects of said sensor observations, said universal health metrics monitors include all or part of said informational representations in second-series observation datasets, (c) measure point operations, wherein said universal health metrics monitors utilize measure points in their locating of selected analytically rich aspects, characteristics, or features of or from sensor observation-derived representations of sensor observations or people who are subjects of sensor observations, said universal health metrics monitors assign appropriate informational representations regarding said measure points, aspects, characteristics, or features of or from said sensor observation-derived representations, wherein all or part of said informational representations are stored or utilized by said universal health metrics monitors in their making of selected health determinations regarding or utilizing said sensor observations or said people who are subjects of said sensor observations, (d) concise datasets operations, wherein said universal health metrics monitors utilize concise datasets in their making of selected health determinations, said concise datasets include selected sensor data or derived data, wherein said selected sensor data comprises informational representation that were selected from sensor observation datasets and said derived data comprises informational representations that were derived from (i) processing selected informational representations from sensor observation datasets, or (ii) processing selected informational representations from derived data, said informational representations from said selected sensor data or said informational representations from said derived data are utilizable by said universal health metrics monitors in their making of selected health determinations regarding or utilizing sensor observations or people who are subjects of said sensor observations' health, and said derived data are derived utilizing tools, methodologies, or programming from a complete spectrum of tools, methodologies, or programming that can be utilized in deriving informational representations from sensor data, or from or for derived data, (e) matching operations, wherein said universal health metrics monitors' matching operations include matching informational representation from second-series observation datasets to comparable informational representation from first-series observation datasets, (f) comparing operations, wherein said universal health metrics monitors' comparing operations include comparing informational representation from second-series observation datasets to comparable informational representation from first-series observation datasets and providing conclusions or determinations from said comparing, (g) determining operations, wherein said universal health metrics monitors utilize conclusions or determinations from comparing operations, or information in their making of said selected health determinations, and (h) reporting operations, wherein said universal health metrics monitors include reporting operations; wherein said universal health metrics monitors provide selected reports regarding or utilizing selected aspects, characteristics, or features of or from all or part of any cycle of utilization of said universal health metrics monitors.

* * * * *

UNITED STATES PATENT AND TRADEMARK OFFICE
CERTIFICATE OF CORRECTION

PATENT NO. : 12,390,111 B2
APPLICATION NO. : 17/984266
DATED : August 19, 2025
INVENTOR(S) : Jeffry David Aronson Page 1 of 1

It is certified that error appears in the above-identified patent and that said Letters Patent is hereby corrected as shown below:

In the Claims

Claim 1, Column 51, Line 34, please delete "As calable" and insert -- A scalable --.

Signed and Sealed this
Fourteenth Day of October, 2025

John A. Squires
*Director of the United States Patent and Trademark Office*